(12) United States Patent
Claus et al.

(10) Patent No.: US 7,323,468 B2
(45) Date of Patent: Jan. 29, 2008

(54) PYRIDOPYRAZINES AND THE USE THEREOF AS KINASE INHIBITORS

(75) Inventors: Eckhard Claus, Frankfurt am Main (DE); Eckhard Günther, Maintal (DE); Irene Seipelt, Offenbach (DE); Ulf R. Rapp, Würzburg (DE); Ludmilla Wixler, Würzburg (DE)

(73) Assignee: AEterna Zentaris GmbH, Frankfurt (DE)

( * ) Notice: Subject to any disclaimer, the term of this patent is extended or adjusted under 35 U.S.C. 154(b) by 143 days.

(21) Appl. No.: 10/851,966

(22) Filed: May 21, 2004

(65) Prior Publication Data

US 2005/0032803 A1 Feb. 10, 2005

Related U.S. Application Data

(60) Provisional application No. 60/473,935, filed on May 28, 2003.

(30) Foreign Application Priority Data

May 23, 2003 (DE) ................ 103 23 345

(51) Int. Cl.
- A01N 43/58 (2006.01)
- A01N 43/60 (2006.01)
- A61K 31/50 (2006.01)
- A61K 31/495 (2006.01)

(52) U.S. Cl. ............... 514/249; 544/117; 544/350

(58) Field of Classification Search ............... None
See application file for complete search history.

(56) References Cited

U.S. PATENT DOCUMENTS 5,424,311 A 6/1995 Billhardt-Troughton et al.

FOREIGN PATENT DOCUMENTS

| JP | 50-053394 | 5/1975 |
|---|---|---|
| JP | 2006137723 | 6/2006 |
| WO | WO 99/17759 | 4/1999 |
| WO | WO 03/024448 A2 | 3/2003 |
| WO | WO/2004/005472 | 1/2004 |
| WO | WO 2004/005472 A2 | 1/2004 |
| WO | WO/2004/030635 | 4/2004 |
| WO | WO/2005/010000 | 2/2005 |
| WO | WO/2005/061519 | 2/2005 |
| WO | WO/2005/056825 | 6/2005 |
| WO | WO/2005/103029 | 11/2005 |
| WO | WO/2005/123698 | 12/2005 |
| WO | WO/2005/123733 | 12/2005 |
| WO | WO/2006/042289 | 4/2006 |
| WO | WO/2006/044823 | 4/2006 |
| WO | WO/2006/059103 | 6/2006 |
| WO | WO/2006/073938 | 7/2006 |
| WO | WO/2006/074147 | 7/2006 |
| WO | WO/2006/076646 | 7/2006 |
| WO | WO/2006/078283 | 7/2006 |
| WO | WO/2006/081178 | 8/2006 |
| WO | WO/2006/081179 | 8/2006 |
| WO | WO/2006/081182 | 8/2006 |
| WO | WO/2006/081264 | 8/2006 |
| WO | WO/2006/081388 | 8/2006 |
| WO | WO/2006/128129 | 11/2006 |
| WO | WO/2006/128172 | 11/2006 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Elliot, Robert D., et al.: The Isomeric Pyridopyrazine from the Reaction of Some Tetraaminopyridines with Pyruvaldehyde and Benzil. In: Isomeric Pyridophyrazines, vol. 33, No. 6, Jun. 1968, 2393-2397.
Temple, Carroll, Rener, Gregory A.: Potential Antimitotic Agents. Synthesis of Some Ethyl Benzopyrazin-7-ylcarbamates, Ethyl Pyrido[3,4-b]pyrazin-7-ylcarbamates, and Ethyl Pyrido[3,4-e]-as-triazin-7-ylcarbamates; J. Med. Chem. 1990, 33, 3044-3050.
Kaye, I. A., Some substituted pyrido(2,3)pyrazines, J. Med. Chem. Bd. 7, 1964, Seiten 240-241.

* cited by examiner

*Primary Examiner*—Zachary C Tucker
(74) *Attorney, Agent, or Firm*—Goodwin Procter LLP

(57) ABSTRACT

The invention relates to novel pyrido[2,3-b]pyrazine derivatives of the general Formula I, their preparation and use as medicaments, in particular for the treatment of malignant and other disorders based on pathological cell proliferations.

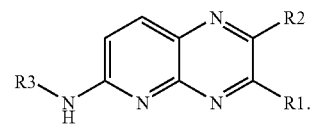

8 Claims, No Drawings

US 7,323,468 B2

PYRIDOPYRAZINES AND THE USE THEREOF AS KINASE INHIBITORS

CROSS-REFERENCE TO RELATED APPLICATIONS

This application claims the benefit of priority to U.S. Provisional Application No. 60/473,935 filed on May 28, 2003 and German Patent Application No. 103 23 345.8 filed on May 23, 2003, which are incorporated herein by reference in their entirety.

FIELD OF THE INVENTION

The invention relates to kinase inhibitors of the pyrido[2,3-b]pyrazine type, the preparation and use thereof as medicaments, in particular for the treatment of malignant and other disorders based on pathological cell proliferation, such as, for example, restenosis, psoriasis, arteriosclerosis and cirrhosis of the liver.

BACKGROUND OF THE INVENTION

Activation of protein kinases is a central event in cellular signal transduction processes. Aberrant kinase activation is observed in various pathological states. Targeted inhibition of such constitutively active kinases is therefore a fundamental therapeutic aim.

The phosphorylation of proteins is generally initiated by extracellular signals and represents a universal mechanism for controlling various cellular events such as, for example, metabolic processes, cell growth, cell migration, cell differentiation, membrane transport and apoptosis. The kinase protein family is responsible for protein phosphorylation. These enzymes catalyse transfer of phosphate to specific substrate proteins. Based on the substrate specificity, the kinases are divided into two main classes, the tyrosine kinases and the serine/threonine kinases. Both the receptor tyrosine kinases and the cytoplasmic tyrosine and serine/threonine kinases are important proteins in cellular signal transduction. Overexpression or degradation of these proteins plays an important part in disorders based on pathological cell proliferations. These include inter alia metabolic disorders, disorder of the connective tissue and of the blood vessels, and malignant and benign oncoses. In tumour initiation and development they frequently occur as oncogens, i.e. as aberrant, constitutively active kinase proteins. The consequences of this excessive kinase activation are, for example, uncontrolled cell growth and reduced cell death. Stimulation of tumour-induced growth factors may also be the cause of overstimulation of kinases. Development of kinase inhibitors is therefore of particular interest for all pathogenic processes influenced by kinases.

Pyrido[2,3-b]pyrazine derivatives substituted in position 6 are widely used as pharmacologically active compounds and as synthons in pharmaceutical chemistry. For example, the patent WO 99/17759 describes pyrido[2,3-b]pyrazines which have in position 6 inter alia alkyl-, aryl- and heteroaryl-substituted carbamates. These compounds are intended to be used to modulate the function of serine-threonine protein kinases.

In addition, the patent WO 03/024448 A2 of Delorme et al. describes amide- and acrylamide-substituted pyrido[2,3-b]pyrazines which also contain carbamates as additional substituents and can be used as histone deacetylase inhibitors for the treatment of disorders of cell proliferation.

A further publication (C. Temple, Jr.; J. Med. Chem. 1990, 3044-3050) describes in one example the synthesis of a 6-ethyl carbamate-substituted pyrido[2,3-b]pyrazine derivative. An antitumour effect is neither disclosed nor obvious. The synthesis of further derivatives of 6-ethyl carbamate-substituted pyrido[2,3-b]pyrazine is described in a publication by R. D. Elliott (J. Org. Chem. 1969, 2393-2397). A biological effect of these compounds is neither described nor obvious. The publication by C. Temple, Jr., J. Med. Chem. 1968, 1216-1218 describes the synthesis and investigation of 6-ethyl carbamate-substituted pyrido[2,3-b]pyrazines as potential antimalarial agents. An antitumour effect is neither disclosed nor obvious.

BRIEF SUMMARY OF THE INVENTION

The invention is therefore directed at generating novel compounds which are suitable as inhibitors of such constitutively active kinases, especially the receptor tyrosine kinases and the cytoplasmic tyrosine and serine/threonine kinases.

DETAILED DESCRIPTION OF THE INVENTION

It has now been found, surprisingly, that novel compounds from the pyrido[2,3-b]pyrazine series which are substituted in position 6 for example by urea, thiourea, guanidine or amidine groups are suitable for producing medicaments and, in particular, for the treatment of malignant and other disorders based on pathological cell proliferations. According to this aspect, the present application describes novel compounds from the pyrido[2,3-b]pyrazine series of the general Formula I

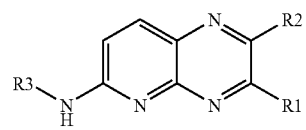

I in which the substituents R1-R3 have the following meaning:

R1 and R2 may be independently of one another:
(i) hydrogen
(ii) hydroxyl
(iii) alkyl, where the alkyl radical is saturated and may consist of 1 to 8 C atoms,
(iv) unsubstituted or substituted aryl, where the aryl radical may have one or more identical or different F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-$NH_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, $NHSO_2$-alkyl, $NHSO_2$-aryl, $NHSO_2$-heteroaryl, $NO_2$, SH, S-alkyl, S-aryl, S-heteroaryl, OH, $OCF_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, OC(O)-alkyl, OC(O)-cycloalkyl, OC(O)-heterocyclyl, OC(O)-aryl, OC(O)-heteroaryl, $OSO_2$-alkyl, $OSO_2$-aryl, $OSO_2$-heteroaryl, C(O)-aryl, C(O)-heteroaryl, $CO_2$H, $CO_2$-alkyl, $CO_2$-cycloalkyl, $CO_2$- heterocyclyl, CO₂-aryl, CO₂-heteroaryl, CO₂-alkyl-cycloalkyl, CO₂-alkyl-heterocyclyl, CO₂-alkyl-aryl, CO₂-alkyl-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)₂, SO₂-alkyl, SO₂-aryl, SO₂NH₂, SO₂NH-alkyl, SO₂NH-aryl, SO₂NH-heteroaryl, SO₃H, SO₂O-alkyl, SO₂O-aryl, alkyl, cycloalkyl, heterocyclyl, aryl or heteroaryl substituents, and the alkyl, cycloalkyl, heterocyclyl, aryl, heteroaryl, alkyl-cycloalkyl, alkyl-heterocyclyl, alkyl-aryl and alkyl-heteroaryl substituents may in turn themselves be substituted, (v) unsubstituted or substituted heteroaryl, where the heteroaryl radical may have one or more identical or different F, Cl, Br, I, CF₃, CN, NH₂, NH-alkyl, NH-cycloalkyl, NH-heterocyclyl, NH-aryl, NH-heteroaryl, N(alkyl)₂, NHC(O)-alkyl, NHC(O)-cycloalkyl, NHC(O)-heterocyclyl, NHC(O)-aryl, NHC(O)-heteroaryl, NHSO₂-alkyl, NHSO₂-aryl, NHSO₂-heteroaryl, NO₂, SH, S-alkyl, S-aryl, OH, OCF₃, O-alkyl, O-cycloalkyl, O-aryl, O-heteroaryl, OC(O)-alkyl, OC(O)-cycloalkyl, OC(O)-heterocyclyl, OC(O)-aryl, OC(O)-heteroaryl, OSO₂-alkyl, OSO₂-cycloalkyl, OSO₂-aryl, OSO₂-heteroaryl, C(O)-alkyl, C(O)-aryl, CO₂H, CO₂-alkyl, CO₂-cycloalkyl, CO₂-heterocyclyl, CO₂-aryl, CO₂-heteroaryl, C(O)—NH₂, C(O)NH-alkyl, C(O)NH-cycloalkyl, C(O)NH-heterocyclyl, C(O)NH-aryl, C(O)NH-heteroaryl, C(O)N(alkyl)₂, SO₂NH₂, SO₂NH-alkyl, SO₂NH-aryl, SO₃H, SO₂O-alkyl, SO₂O-aryl, alkyl, cycloalkyl, heterocyclyl, aryl or heteroaryl substituents, and the alkyl, cycloalkyl, heterocyclyl, aryl and heteroaryl substituents may in turn themselves be substituted.

R3 may be:

—C(Y)NR4R5, where Y is O, S and R4 and R5 are independently of one another (i) hydrogen, (ii) unsubstituted or substituted alkyl, where the alkyl radical may have one or more identical or different F, Cl, Br, I, CF₃, CN, NH₂, NH-alkyl, NH-cycloalkyl, NH-heterocyclyl, NH-aryl, NH-heteroaryl, NH-alkyl-aryl, NH-alkyl-heteroaryl, N(alkyl)₂, NHC(O)-alkyl, NHC(O)-cycloalkyl, NHC(O)-heterocyclyl, NHC(O)-aryl, NHC(O)-heteroaryl, NHSO₂-alkyl, NHSO₂-cycloalkyl, NHSO₂-aryl, NHSO₂-heteroaryl, NO₂, SH, S-alkyl, S-cycloalkyl, S-heterocyclyl, S-aryl, S-heteroaryl, OH, OCF₃, O-alkyl, O-cycloalkyl, O-heterocyclyl, O-aryl, O-heteroaryl, O-alkyl-cycloalkyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OSO₂-alkyl, OSO₂-cycloalkyl, OSO₂-aryl, OSO₂-heteroaryl, C(O)-alkyl, C(O)-aryl, CO₂H, CO₂-alkyl, CO₂-cycloalkyl, CO₂-heterocyclyl, CO₂-aryl, CO₂-heteroaryl, CO₂-alkyl-cycloalkyl, CO₂-alkyl-heterocyclyl, CO₂-alkyl-aryl, CO₂-alkyl-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)₂, C(O)N(cycloalkyl)₂, C(O)N(aryl)₂, C(O)N(heteroaryl)₂, SO-alkyl, SO-aryl, SO₂-alkyl, SO₂-aryl, SO₂NH₂, SO₃H, alkyl, cycloalkyl, heterocyclyl, aryl or heteroaryl substituents, (iii) unsubstituted or substituted cycloalkyl, where the cycloalkyl radical may have one or more identical or different F, Cl, Br, I, NH₂, NH-alkyl, NH-cycloalkyl, NH-heterocyclyl, NH-aryl, NH-heteroaryl, NH-alkyl-aryl, NH-alkyl-heteroaryl, N(alkyl)₂, NHC(O)-alkyl, NHC(O)-cycloalkyl, NHC(O)-heterocyclyl, NHC(O)-aryl, NHC(O)-heteroaryl, NHSO₂-alkyl, NHSO₂-cycloalkyl, NHSO₂-aryl, NHSO₂-heteroaryl, OH, O-alkyl, O-cycloalkyl, O-heterocyclyl, O-aryl, O-heteroaryl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OSO₂-alkyl, OSO₂-cycloalkyl, OSO₂-aryl, OSO₂-heteroaryl, CO₂H, CO₂-alkyl, CO₂-cycloalkyl, CO₂-heterocyclyl, CO₂-aryl, CO₂-heteroaryl, C(O)—NH₂, C(O)NH-aryl, C(O)NH-cycloalkyl, C(O)NH-heterocyclyl, C(O)NH-aryl, C(O)NH-heteroaryl, C(O)NH-alkyl-aryl, C(O)NH-alkyl-heteroaryl, C(O)N(alkyl)₂, alkyl or aryl substituents, (iv) unsubstituted or substituted heterocyclyl, where the heterocyclyl radical may have one or more identical or different OH, O-alkyl, O-aryl, NH-alkyl, NH-aryl, alkyl, alkyl-aryl or aryl substituents, (v) unsubstituted or substituted aryl, where the aryl radical may have one or more identical or different F, Cl, Br, I, CF₃, CN, NH₂, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-NH₂, NH-alkyl-OH, N(alkyl)₂, NHC(O)-alkyl, NHC(O)-cycloalkyl, NHC(O)-heterocyclyl, NHC(O)-aryl, NHC(O)-heteroaryl, NHSO₂-alkyl, NHSO₂-aryl, NHSO₂-heteroaryl, NO₂, SH, S-alkyl, S-cycloalkyl, S-heterocyclyl, S-aryl, S-heteroaryl, OH, OCF₃, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, OC(O)-alkyl, OC(O)-cycloalkyl, OC(O)-heterocyclyl, OC(O)-aryl, OC(O)-heteroaryl, OSO₂-alkyl, OSO₂-cycloalkyl, OSO₂-aryl, OSO₂-heteroaryl, C(O)-alkyl, C(O)-aryl, C(O)-heteroaryl, CO₂H, CO₂-alkyl, CO₂-cycloalkyl, CO₂-heterocyclyl, CO₂-aryl, CO₂-heteroaryl, CO₂-alkyl-cycloalkyl, CO₂-alkyl-heterocyclyl, CO₂-alkyl-aryl, CO₂-alkyl-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)₂, C(O)N(cycloalkyl)₂, C(O)N(aryl)₂, C(O)N(heteroaryl)₂, SO-alkyl, SO-aryl, SO₂-alkyl, SO₂-aryl, SO₂NH₂, SO₂NH-alkyl, SO₂NH-aryl, SO₂NH-heteroaryl, SO₃H, SO₂O-alkyl, SO₂O-aryl, SO₂O-heteroaryl, alkyl, cycloalkyl, heterocyclyl, aryl or heteroaryl substituents, (vi) unsubstituted or substituted heteroaryl, where the heteroaryl radical may have one or more identical or different F, Cl, Br, I, CF₃, CN, NH₂, NH-alkyl, NH-cycloalkyl, NH-heterocyclyl, NH-aryl, NH-heteroaryl, NH-alkyl-aryl, NH-alkyl-heteroaryl, N(alkyl)₂, NHC(O)-alkyl, NHC(O)-cycloalkyl, NHC(O)-heterocyclyl, NHC(O)-aryl, NHC(O)-heteroaryl, NHSO₂-alkyl, NHSO₂-aryl, NHSO₂-heteroaryl, NO₂, SH, S-alkyl, S-aryl, OH, OCF₃, O-alkyl, O-cycloalkyl, O-heterocyclyl, O-aryl, O-heteroaryl, OC(O)-alkyl, OC(O)-cycloalkyl, OC(O)-heterocyclyl, OC(O)-aryl, OC(O)-heteroaryl, OSO₂-alkyl, OSO₂-cycloalkyl, OSO₂-aryl, OSO₂-heteroaryl, C(O)-alkyl, C(O)-aryl, C(O)-heteroaryl, CO₂H, CO₂-alkyl, CO₂-cycloalkyl, CO₂-heterocyclyl, CO₂-aryl, CO₂-heteroaryl, CO₂-alkyl-cycloalkyl, CO₂-alkyl-heterocyclyl, CO₂-alkyl-aryl, CO₂-alkyl-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)₂, C(O)N(cycloalkyl)₂, C(O)N(aryl)₂, C(O)N(heteroaryl)₂, SO₂- alkyl, SO₂-aryl, SO₂NH₂, SO₂NH-alkyl, SO₂NH-aryl, SO₂NH-heteroaryl, SO₃H, SO₂O-alkyl, SO₂O-aryl, SO₂O-heteroaryl, alkyl, cycloalkyl, heterocyclyl, aryl or heteroaryl substituents, (vii) or R4 and R5 together are cycloalkyl or heterocyclyl, are —C(Y)NR6R7, where Y is NH and R6 and R7 are independently of one another (i) hydrogen, (ii) unsubstituted or substituted alkyl, where the alkyl radical may have one or more identical or different F, Cl, Br, I, CF₃, CN, NH₂, NH-alkyl, NH-cycloalkyl, NH-heterocyclyl, NH-aryl, NH-heteroaryl, NH-alkyl-aryl, NH-alkyl-heteroaryl, N(alkyl)₂, NHC(O)-alkyl, NHC(O)-cycloalkyl, NHC(O)-heterocyclyl, NHC(O)-aryl, NHC(O)-heteroaryl, NHSO₂-alkyl, NHSO₂-cycloalkyl, NHSO₂-aryl, NHSO₂-heteroaryl, NO₂, SH, S-alkyl, S-cycloalkyl, S-heterocyclyl, S-aryl, S-heteroaryl, OH, OCF₃, O-alkyl, O-cycloalkyl, O-heterocyclyl, O-aryl, O-heteroaryl, O-alkyl-cycloalkyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OSO₂-alkyl, OSO₂-cycloalkyl, OSO₂-aryl, OSO₂-heteroaryl, C(O)-alkyl, C(O)-aryl, CO₂H, CO₂-alkyl, CO₂-cycloalkyl, CO₂-heterocyclyl, CO₂-aryl, CO₂-heteroaryl, CO₂-alkyl-cycloalkyl, CO₂-alkyl-heterocyclyl, CO₂-alkyl-aryl, CO₂-alkyl-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)₂, C(O)N(cycloalkyl)₂, C(O)N(aryl)₂, C(O)N(heteroaryl)₂, SO-alkyl, SO-aryl, SO₂-alkyl, SO₂-aryl, SO₂NH₂, SO₃H, alkyl, cycloalkyl, heterocyclyl, aryl or heteroaryl substituents, (iii) unsubstituted or substituted cycloalkyl, where the cycloalkyl radical may have one or more identical or different F, Cl, Br, I, NH₂, NH-alkyl, NH-cycloalkyl, NH-heterocyclyl, NH-aryl, NH-heteroaryl, NH-alkyl-aryl, NH-alkyl-heteroaryl, N(alkyl)₂, NHC(O)-alkyl, NHC(O)-cycloalkyl, NHC(O)-heterocyclyl, NHC(O)-aryl, NHC(O)-heteroaryl, NHSO₂-alkyl, NHSO₂-cycloalkyl, NHSO₂-aryl, NHSO₂-heteroaryl, OH, O-alkyl, O-cycloalkyl, O-heterocyclyl, O-aryl, O-heteroaryl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OSO₂-alkyl, OSO₂Cycloalkyl, OSO₂-aryl, OSO₂-heteroaryl, CO₂H, CO₂-alkyl, CO₂-cycloalkyl, CO₂-heterocyclyl, CO₂-aryl, CO₂-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-aryl, C(O)NH-alkyl-heteroaryl, C(O)N(alkyl)₂, alkyl or aryl substituents, (iv) unsubstituted or substituted heterocylyl, where the heterocyclyl radical may have one or more identical or different OH, O-alkyl, O-aryl, NH-alkyl, NH-aryl, alkyl or aryl substituents, (v) unsubstituted or substituted aryl, where the aryl radical may have one or more identical or different F, Cl, Br, I, CF₃, CN, NH₂, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-NH₂, NH-alkyl-OH, N(alkyl)₂, NHC(O)-alkyl, NHC(O)-cycloalkyl, NHC(O)-heterocyclyl, NHC(O)-aryl, NHC(O)-heteroaryl, NHSO₂-alkyl, NHSO₂-aryl, NHSO₂-heteroaryl, NO₂, SH, S-alkyl, S-cycloalkyl, S-heterocyclyl, S-aryl, S-heteroaryl, OH, OCF₃, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, OC(O)-alkyl, OC(O)-cycloalkyl, OC(O)-heterocyclyl, OC(O)-aryl, OC(O)-heteroaryl, OSO₂-alkyl, OSO₂-cycloalkyl, OSO₂-aryl, OSO₂-heteroaryl, C(O)-alkyl, C(O)-aryl, C(O)-heteroaryl, CO₂H, CO₂-alkyl, CO₂-cycloalkyl, CO₂-heterocyclyl, CO₂-aryl, CO₂-heteroaryl, CO₂-alkyl-cycloalkyl, CO₂-alkyl-heterocyclyl, CO₂-alkyl-aryl, CO₂-alkyl-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)₂, C(O)N(cycloalkyl)₂, C(O)N(aryl)₂, C(O)N(heteroaryl)₂, SO-alkyl, SO-aryl, SO₂-alkyl, SO₂-aryl, SO₂NH₂, SO₂NH-alkyl, SO₂NH-aryl, SO₂NH-heteroaryl, SO₃H, SO₂O-alkyl, SO₂O-aryl, SO₂O-heteroaryl, alkyl, cycloalkyl, heterocyclyl, aryl or heteroaryl substituents, (vi) unsubstituted or substituted heteroaryl, where the heteroaryl radical may have one or more identical or different F, Cl, Br, I, CF₃, CN, NH₂, NH-alkyl, NH-cycloalkyl, NH-heterocyclyl, NH-aryl, NH-heteroaryl, NH-alkyl-aryl, NH-alkyl-heteroaryl, N(alkyl)₂, NHC(O)-alkyl, NHC(O)-cycloalkyl, NHC(O)-heterocyclyl, NHC(O)-aryl, NHC(O)-heteroaryl, NHSO₂-alkyl, NHSO₂-cycloalkyl, NHSO₂-heteroaryl, NO₂, SH, S-alkyl, S-aryl, OH, OCF₃, O-alkyl, O-cycloalkyl, O-heterocyclyl, O-aryl, O-heteroaryl, OC(O)-alkyl, OC(O)-cycloalkyl, OC(O)-heterocyclyl, OC(O)-aryl, OC(O)-heteroaryl, OSO₂-alkyl, OSO₂-cycloalkyl, OSO₂-aryl, OSO₂-heteroaryl, C(O)-alkyl, C(O)-aryl, C(O)-heteroaryl, CO₂H, CO₂-alkyl, CO₂-cycloalkyl, CO₂-heterocyclyl, CO₂-aryl, CO₂-heteroaryl, CO₂-alkyl-cycloalkyl, CO₂-alkylheterocyclyl, CO₂-alkyl-aryl, CO₂-alkyl-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)₂, C(O)N(cycloalkyl)₂, C(O)N(aryl)₂, C(O)N(heteroaryl)₂, SO₂-alkyl, SO₂-aryl, SO₂NH₂, SO₂NH-alkyl, SO₂NH-aryl, SO₂NH-heteroaryl, SO₃H, SO₂O-alkyl, SO₂O-aryl, SO₂O-heteroaryl, alkyl, cycloalkyl, heterocyclyl, aryl or heteroaryl substituents, (vii) or R6 and R7 together are cycloalkyl or heterocyclyl, are —C(NR8)R9 where R8 is H and R9 is (i) unsubstituted or substituted alkyl, where the alkyl radical may have one or more identical or different F, Cl, Br, I, CF₃, NH₂, NH-alkyl, NH-cycloalkyl, NH-heterocyclyl, NH-aryl, NH-heteroaryl, NH-alkyl-aryl, NH-alkyl-heteroaryl, N(alkyl)₂, NHC(O)-alkyl, NHC(O)-cycloalkyl, NHC(O)-heterocyclyl, NHC(O)-aryl, NHC(O)-heteroaryl, NHSO₂-alkyl, NHSO₂-cycloalkyl, NHSO₂-aryl, NHSO₂-heteroaryl, NO₂, SH, S-alkyl, S-cycloalkyl, S-heterocyclyl, S-aryl, S-heteroaryl, OH, OCF₃, O-alkyl, O-cycloalkyl, O-heterocyclyl, O-aryl, O-heteroaryl, O-alkyl-cycloalkyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OSO₂-alkyl, OSO₂-cycloalkyl, OSO₂-aryl, OSO₂-heteroaryl, C(O)-alkyl, C(O)-aryl, CO₂H, CO₂-alkyl, CO₂-cycloalkyl, CO₂-heterocyclyl, CO₂-aryl, CO₂-heteroaryl, CO₂-alkyl-cycloalkyl, CO₂-alkyl-heterocyclyl, CO₂-alkyl-aryl, CO₂-alkyl-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)₂, C(O)N(cycloalkyl)₂, C(O)N(aryl)₂, C(O)N(heteroaryl)₂, SO-alkyl, SO-aryl, SO₂- alkyl, SO$_2$-aryl, SO$_2$NH$_2$, SO$_3$H, alkyl, cycloalkyl, heterocyclyl, aryl or heteroaryl substituents, (ii) unsubstituted or substituted cycloalkyl, where the cycloalkyl radical may have one or more identical or different F, Cl, Br, I, NH$_2$, NH-alkyl, NH-cycloalkyl, NH-heterocyclyl, NH-aryl, NH-heteroaryl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHSO$_2$-alkyl, NHSO$_2$-cycloalkyl, NHSO$_2$-aryl, NHSO$_2$-heteroaryl, OH, O-alkyl, O-cycloalkyl, O-heterocyclyl, O-aryl, O-heteroaryl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OSO$_2$-alkyl, OSO$_2$-cycloalkyl, OSO$_2$-aryl, OSO$_2$-heteroaryl, CO$_2$H, CO$_2$-alkyl, CO$_2$-cycloalkyl, CO$_2$-heterocyclyl, CO$_2$-aryl, CO$_2$-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-aryl, C(O)NH-alkyl-heteroaryl, C(O)N(alkyl)$_2$, alkyl or aryl substituents, (iii) unsubstituted or substituted heterocyclyl, where the heterocyclyl radical may have one or more identical or different OH, O-alkyl, O-aryl, NH-alkyl, NH-aryl, alkyl or aryl substituents, (iv) unsubstituted or substituted aryl, where the aryl radical may have one or more identical or different F, Cl Br, I, CF$_3$, NH$_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-NH$_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHSO$_2$-alkyl, NHSO$_2$-aryl, NHSO$_2$-heteroaryl, NO$_2$, SH, S-alkyl, S-cycloalkyl, S-heterocyclyl, S-aryl, S-heteroaryl, OH, OCF$_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, OC(O)-alkyl, OC(O)-cycloalkyl, OC(O)-heterocyclyl, OC(O)-aryl, OC(O)-heteroaryl, OSO$_2$-alkyl OSO$_2$-cycloalkyl, OSO$_2$-aryl, OSO$_2$-heteroaryl, C(O)-alkyl, C(O)-aryl, C(O)-heteroaryl, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkyl-heterocyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, SO$_2$-alkyl, SO$_2$-aryl, SO$_2$NH$_2$, SO$_2$NH-alkyl, SO$_2$NH-aryl, SO$_2$NH-heteroaryl, SO$_3$H, SO$_2$O-alkyl, SO$_2$O-aryl, SO$_2$O-heteroaryl, alkyl, cycloalkyl, heterocyclyl, aryl or heteroaryl substituents, (v) unsubstituted or substituted heteroaryl, where the heteroaryl radical may have one or more identical or different F, Cl, Br, I, CF$_3$, NH$_2$, NH-alkyl, NH-cycloalkyl, NH-heterocyclyl, NH-aryl, NH-heteroaryl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHSO$_2$-alkyl, NHSO$_2$-aryl, NHSO$_2$-heteroaryl, NO$_2$, SH, S-alkyl, S-aryl, OH, OCF$_3$, O-alkyl, O-cycloalkyl, O-heterocyclyl, O-aryl, O-heteroaryl, OC(O)-alkyl, OC(O)-cycloalkyl, OC(O)-heterocyclyl, OC(O)-aryl, OC(O)-heteroaryl, OSO$_2$-alkyl, OSO$_2$-cycloalkyl, OSO$_2$-aryl, OSO$_2$-heteroaryl, C(O)-alkyl, C(O)-aryl, C(O)-heteroaryl, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkyl-heterocyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO$_2$-alkyl, SO$_2$-aryl, SO$_2$NH$_2$, SO$_2$NH-alkyl, SO$_2$NH-aryl, SO$_2$NH-heteroaryl, SO$_3$H, SO$_2$O-alkyl, SO$_2$O-aryl, SO$_2$O-heteroaryl, alkyl, cycloalkyl, heterocyclyl, aryl or heteroaryl substituents.

The term "alkyl" includes for the purpose of this invention acyclic saturated or unsaturated hydrocarbon radicals which may be branched or straight-chain and unsubstituted or mono- or polysubstituted, having 1 to 8 C atoms, i.e. $C_{1-8}$-alkanyls, $C_{2-8}$-alkenyls and $C_{2-8}$-alkynyls. In this connection, alkenyls have at least one C—C double bond and alkynyls have at least one C—C triple bond. Alkyl is preferably selected from the group comprising methyl, ethyl, n-propyl, 2-propyl, n-butyl, sec-butyl, tert-butyl, n-pentyl, isopentyl, neopentyl, n-hexyl, 2-hexyl, n-octyl, ethylenyl (vinyl), ethynyl, propenyl (—CH$_2$CH=CH$_2$; —CH=CH—CH$_3$, —C(=CH$_2$)—CH$_3$), propynyl (—CH$_2$—C≡CH, —C≡C—CH$_3$), butenyl, butynyl, pentenyl, pentynyl, hexenyl, hexynyl, heptenyl, heptynyl, octenyl and octynyl.

The term "cycloalkyl" means for the purposes of this invention cyclic hydrocarbon radicals having 3-12 carbon atoms, which may be saturated or unsaturated. It is possible for the linkage to the compounds of the general structure I to take place via any possible ring member of the cycloalkyl radical. The cycloalkyl radical may also be part of a bi- or polycyclic system.

The term "heterocyclyl" stands for a 3-, 4-, 5-, 6-, 7- or 8-membered cyclic organic radical which comprises at least 1, where appropriate 2, 3, 4 or 5, heteroatoms, the heteroatoms being identical or different and the cyclic radical being saturated or unsaturated, but not aromatic. It is possible for the linkage to the compounds of the general structure I to take place via any possible ring member of the heterocyclyl radical. The heterocycle may also be part of a bi- or polycyclic system. Preferred heteroatoms are nitrogen, oxygen and sulphur. It is preferred for the heterocyclyl radical to be selected from the group comprising tetrahydrofuryl, tetrahydropyranyl, pyrrolidinyl, piperidinyl, piperazinyl and morpholinyl.

The term "aryl" means for the purpose of this invention aromatic hydrocarbons, inter alia phenyls, naphthyls and anthracenyls. The radicals may also be fused to other saturated, (partially) unsaturated or aromatic ring systems. It is possible for the linkage to the compounds of the general structure I to take place via any possible ring member of the aryl radical.

The term "heteroaryl" stands for a 5-, 6- or 7-membered cyclic aromatic radical which comprises at least 1, where appropriate also 2, 3, 4 or 5, heteroatoms, the heteroatoms being identical or different. It is possible for the linkage to the compounds of the general structure I to take place via any possible ring member of the heteroaryl radical. The heterocycle may also be part of a bi- or polycyclic system. Preferred heteroatoms are nitrogen, oxygen and sulphur. It is preferred for the heteroaryl radical to be selected from the group comprising pyrrolyl, furyl, thienyl, thiazolyl, oxazolyl, isoxazolyl, pyrazolyl, imidazolyl, pyridinyl, pyrimidinyl, pyridazinyl, pyrazinyl, phthalazinyl, indolyl, indazolyl, indolizinyl, quinolinyl, isoquinolinyl, quinoxalinyl, quinazolinyl, carbazolyl, phenazinyl, phenothiazinyl, acridinyl.

The terms "alkyl-cycloalkyl", "alkyl-heterocyclyl", "alkyl-aryl" or "alkyl-heteroaryl" means for the purposes of the present invention that alkyl and cycloalkyl, heterocyclyl, aryl and heteroaryl have the meanings defined above, and the cycloalkyl, heterocyclyl, aryl or heteroaryl radical is linked via a $C_{1-8}$-alkyl group to the compounds of the general structure I.

The term substituted in connection with "alkyl", "cycloalkyl", "heterocyclyl", "aryl", "heteroaryl", "alkyl-cycloalkyl", "alkyl-heterocyclyl", "alkyl-aryl", and "alkyl-heteroaryl" means for the purposes of this invention, unless explicitly defined above, replacement of one or more hydrogen radicals by F, Cl, Br, I, CN, $CF_3$, $NH_2$, NH-alkyl, NH-aryl, $N(alkyl)_2$, $NO_2$, SH, S-alkyl, OH, $OCF_3$, O-alkyl, O-aryl, CHO, $CO_2H$, $SO_3H$ or alkyl. The substituents may be identical or different, and the substitution may take place at any possible position of the alkyl, cycloalkyl, heterocyclyl, aryl and heteroaryl radical.

Radicals substituted more than once mean those which are substituted more than once, e.g. twice or three times, either on different or on the same atoms, for example three times on the same C atom as in the case of $CF_3$, —$CH_2CF_3$, or in different sites as in the case of —CH(OH)—CH=CH—$CHCl_2$. Substitution more than once can take place with identical or different substituents.

Where the compounds of the invention of the general Formula I have at least one centre of asymmetry, they may exist in the form of their racemates, in the form of the pure enantiomers and/or diastereomers or in the form of mixtures of these enantiomers and/or diastereomers. Any mixing ratio of the stereoisomers in the mixtures is possible.

Thus, for example, the compounds of the invention of the general Formula I which have one or more centres of chirality and which occur as racemates can be separated by methods known per se into their optical isomers, i.e. enantiomers or diastereomers. The separation can take place by column separation on chiral phases or by recrystallization from an optically active solvent or with use of an optically active acid or base or through derivatization with an optically active reagent such as, for example, an optically active alcohol, and subsequent elimination of the radical.

Where possible, the compounds of the invention may exist in the form of tautomers.

The compounds of the invention of the general Formula I may, if they contain a sufficiently basic group such as, for example, a primary, secondary or tertiary amine, be converted with inorganic and organic acids into their physiologically tolerated salts. The pharmaceutically acceptable salts of the compounds of the invention of the general structure I are preferably formed with hydrochloric acid, hydrobromic acid, sulphuric acid, phosphoric acid, methanesulphonic acid, p-toluenesulphonic acid, carbonic acid, formic acid, acetic acid, trifluoroacetic acid, sulphoacetic acid, oxalic acid, malonic acid, maleic acid, succinic acid, tartaric acid, racemic acid, malic acid, embonic acid, mandelic acid, fumaric acid, lactic acid, citric acid, glutamic acid or aspartic acid. The salts which are formed are, inter alia, hydrochlorides, hydrobromides, sulphates, bisulphates, phosphates, methanesulphonates, tosylates, carbonates, bicarbonates, formates, acetates, triflates, sulphoacetates, oxalates, malonates, maleates, succinates, tartrates, malates, embonates, mandelates, fumarates, lactates, citrates, glutamates and aspartates. The stoichiometry of the salts which are formed of the compounds of the invention may moreover be integral or nonintegral multiples of one.

The compounds of the invention of the general Formula I may, if they contain a sufficiently acidic group such as a carboxyl group, be converted with inorganic and organic bases into their physiologically tolerated salts. Examples of suitable inorganic bases are sodium hydroxide, potassium hydroxide, calcium hydroxide, and of organic bases are ethanolamine, diethanolamine, triethanolamine, cyclohexylamine, dibenzylethylenediamine and lysine. The stoichiometry of the salts which are formed of the compounds of the invention may moreover be integral or nonintegral multiples of one.

Preference is likewise given to solvates and, in particular, hydrates of the compounds of the invention which can be obtained for example by crystallization from a solvent or from aqueous solution. It is possible in these cases for one, two, three or any number of solvate or water molecules to combine with the compounds of the invention to give solvates and hydrates.

It is known that chemical substances form solids in various order states which are referred to as polymorphic forms or modifications. The various modifications of a polymorphic substance may vary widely in their physical properties. The compounds of the invention of the general Formula I can exist in various polymorphic forms, and certain modifications may be metastable.

The processes for preparing substituted pyrido[2,3-b]pyrazines of the invention are explained below.

The compounds of the general Formula I can be obtained as shown in the following schemes (scheme 1 and 2):

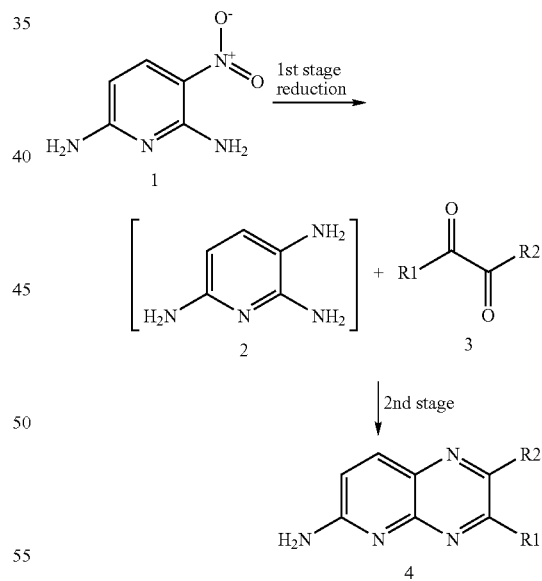

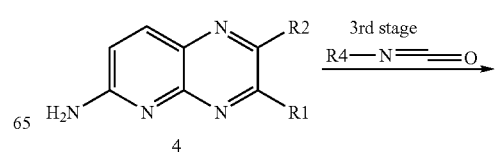

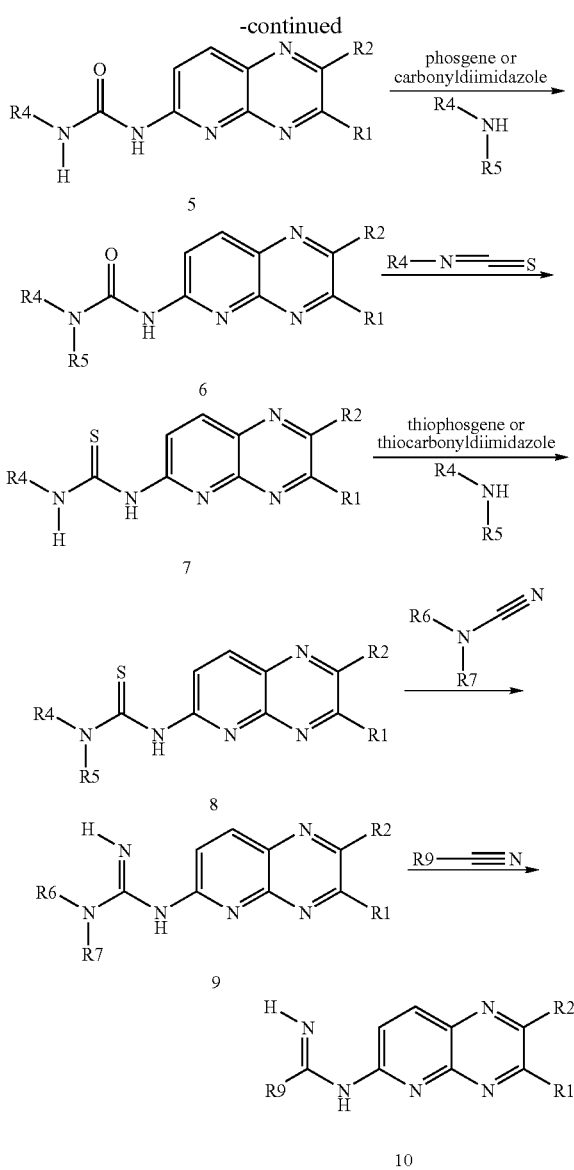

The starting compounds are either commercially available or can be prepared by procedures known per se. Precursors 1 and 4 are valuable intermediates for the preparation of the pyridopyrazines of the invention of the general Formula I.

For the preparation of the starting compounds and target compounds, reference may be made for example to the following primary literature, the contents of which are herein incorporated by reference in their entirety.

1) Houben-Weyl, Methoden der Organischen Chemie, volume 4/1a, pp. 343-350
2) Houben-Weyl, Methoden der Organischen Chemie, 4th edition, volume E 7b (part 2), p. 579; Degussa GB 1184848 (1970); S. Seko, et al. EP 735025 (1996)
3) D. Catarzi, et al.; *J. Med. Chem.* 1996, 1330-1336; J. K. Seydel, et al.; *J. Med. Chem.* 1994, 3016-3022
4) Houben-Weyl, Methods of Organic Chemistry, volume E 9c, pp. 231-235
5) A. M. Thompson, et al. *J. Med. Chem.* 2000, 4200-4211
6) G. Heinisch, et al. *Arch. Pharm.* 1997, 207-210
7) N. A. Dales, et al. *Org. Lett.* 2001, 2313-2316; G. Dannhardt, et al. *Arch. Pharm.* 2000, 267-274
8) M. L. Mussous, et al. *Tetrahedron* 1999, 4077-4094; A. Kling, et al. *Bioorg. Med. Chem. Lett.* 2002, 441-446
9) I. K. Khanna, et al.; *J. Med. Chem.* 2000, 3168-3185
10) L. Younghee, et al.; *Bioorg. Med. Chem. Lett.* 2000, 2771-2774; N. L. Reddy et al.; *J. Med. Chem.* 1998, 3298-3302

General Method for the Preparation of the Compounds of the General Formula I:

1st Stage 2,6-Diamino-3-nitropyridine is dissolved in a polar organic solvent such as, for example, methanol, ethanol, dimethylformamide or dioxane, alone or in a combination of two of these solvents. After addition of a catalyst, for example Raney nickel, palladium on carbon or platinum(IV) dioxide, the reaction mixture is put under a hydrogen atmosphere, adjusting a pressure between 1 and 5 bar. The reaction mixture is left to react in a temperature range between 20° C. and 60° C. for several hours, for example 1-16 hours. After the reaction is complete, the insoluble residues are filtered off, it being possible for the filter medium to consist for example of silica gel, Celite or commercially available glass fibre filters, and washed with the appropriate solvent. The crude product is used in solution, without further purification, for the next reaction.

2nd Stage

The 1,2-dione derivative is introduced into an organic solvent, for example methanol, ethanol, dioxane, toluene or dimethylformamide. 2,3,6-Triaminopyridine is added immediately after reduction as solution of its crude product in one of the abovementioned solvents to the introduced 1,2-dione, where appropriate with addition of an acid such as, for example, acetic acid, or of a base, for example potassium hydroxide. The reaction mixture is left to react in a temperature range from 20° C. to 80° C. for some time, for example 20 minutes to 40 hours. After the reaction is complete, any precipitate which has separated out is filtered off, it being possible for the filter medium to consist for example of commercially available filter paper, and washed with the appropriate solvent, and the remaining solid is dried in vacuo, or the reaction mixture is freed of solvent in vacuo. On use of dimethylformamide, the reaction mixture is stirred into a large amount of water, and the precipitate which has separated out is filtered off, or the aqueous phase is extracted with a suitable organic solvent, and the organic phases are concentrated in vacuo. The remaining crude product is purified by recrystallization from a suitable solvent, for example ethanol, or by column or flash chromatography on silica gel or alumina. A mixture of methanol and dichloromethane is used for example as mobile phase.

3rd Stage

Following the basic process it is possible to convert in subsequent reactions the products resulting from the basic process into subsequent products of the invention of the Formula I in a procedure known to the skilled person.

Thus, if the product is to be a derivative of the compound 5 as shown in scheme 2, the reaction product 4 after completion of the basic reaction can be reacted with an appropriate isocyanate and, where appropriate, a suitable base, preferably sodium hydride, potassium hexamethyldisilazide, triethylamine or potassium carbonate, in a suitable inert solvent such as, for example, dimethylformamide, acetonitrile, tetrahydrofuran, dichloromethane, chloroform, 1,2-dichloroethane or dioxane. The reaction mixture is left to react in a temperature range between 0 and 80° C. for several hours, for example 1-24 hours. After the reaction is complete, any precipitate which has separated out is filtered off, it being possible for the filter medium to consist for example of commercially available filter paper, and washed with the appropriate solvent, and the remaining solid is dried in vacuo, or the reaction mixture is freed of solvent in vacuo. On use of dimethylformamide, the reaction mixture is stirred into a large amount of water, and the precipitate which has separated out is filtered off, or the aqueous phase is extracted with a suitable organic solvent and the organic phases are concentrated in vacuo. The remaining crude product is purified by recrystallization from a suitable solvent, for example ethanol or toluene, or by column or flash chromatography on silica gel or alumina. A mixture of methanol and dichloromethane is used for example as mobile phase.

An alternative possibility if the product is to be a derivative of the compound 6 shown in scheme 2 is, after completion of the basic reaction, to react the reaction product 4 with phosgene or carbonyldiimidazole and an appropriate amine in a suitable inert solvent such as, for example, tetrahydrofuran, toluene, dichloromethane or acetonitrile. A suitable base is used where appropriate, preferably pyridine, sodium bicarbonate, triethylamine, N-methylmorpholine or sodium acetate. The reaction mixture is left to react in a temperature range between 0 and 60° C. for some time, for example 15 minutes to 24 hours. After the reaction is complete, any precipitate which has separated out is filtered off, it being possible for the filter medium to consist for example of commercially available filter paper, and washed with the appropriate solvent, and the remaining solid is dried in vacuo, or the reaction mixture is freed of solvent in vacuo. On use of dimethylformamide, the reaction mixture is stirred into a large amount of water, and the precipitate which has separated out is filtered off, or the aqueous phase is extracted with a suitable organic solvent and the organic phases are concentrated in vacuo. The remaining crude product is purified by recrystallization from a suitable solvent, for example ethanol or ethyl acetate, or by column or flash chromatography on silica gel or alumina. A mixture of methanol and dichloromethane is used for example as mobile phase.

Thus, if the product is to be a derivative of the compound 7 shown in scheme 2, the reaction product 4 after completion of the basic reaction can be reacted with an appropriate isothiocyanate and, where appropriate, a suitable base, preferably sodium hydride, triethylamine or pyridine, in a suitable inert solvent such as, for example, dimethylformamide, tetrahydrofuran, acetone or toluene. The reaction mixture is left to react in a temperature range between 0 and 115° C. for some time, for example 30 minutes to 90 hours. After the reaction is complete, any precipitate which has separated out is filtered off, it being possible for the filter medium to consist for example of commercially available filter paper, and washed with the appropriate solvent, and the remaining solid is dried in vacuo, or the reaction mixture is freed of solvent in vacuo. On use of dimethylformamide, the reaction mixture is stirred into a large amount of water, and the precipitate which has separated out is filtered off, or the aqueous phase is extracted with a suitable organic solvent and the organic phases are concentrated in vacuo. The remaining crude product is purified by recrystallization from a suitable solvent, for example ethanol or ethyl acetate, or by column or flash chromatography on silica gel or alumina. A mixture of methanol and dichloromethane is used for example as mobile phase.

An alternative possibility if the product is to be a derivative of the compound 8 shown in scheme 2 is, after completion of the basic reaction, to react the reaction product 4 with thiophosgene or thiocarbonyldiimidazole and an appropriate amine in a suitable inert solvent such as, for example, tetrahydrofuran, toluene, dichloromethane, ethanol or acetonitrile. A suitable base is used where appropriate, preferably pyridine, sodium bicarbonate, potassium carbonate, triethylamine or imidazole. The reaction mixture is left to react in a temperature range between −10 and 80° C. for several hours, for example 1 to 24 hours. After the reaction is complete, any precipitate which has separated out is filtered off, it being possible for the filter medium to consist for example of commercially available filter paper, and washed with the appropriate solvent, and the remaining solid is dried in vacuo, or the reaction mixture is freed of solvent in vacuo. On use of dimethylformamide, the reaction mixture is stirred into a large amount of water, and the precipitate which has separated out is filtered off, or the aqueous phase is extracted with a suitable organic solvent and the organic phases are concentrated in vacuo. The remaining crude product is purified by recrystallization from a suitable solvent, for example ethanol or ethyl acetate, or by column or flash chromatography on silica gel or alumina. A mixture of ethyl acetate and hexane is used for example as mobile phase.

Thus, if the product is to be a derivative of compound 9 shown in scheme 2, the reaction product 4 after completion of the basic reaction can be reacted with an appropriate amino nitrile and, where appropriate, a suitable base, preferably triethylamine, or a suitable acid, preferably hydrochloric acid, in a suitable inert solvent such as, for example, acetone, toluene, chlorobenzene, ethanol, tetrahydrofuran or dimethyl sulphoxide. The reaction mixture is left to react in a temperature range between 20 and 135° C. for several hours, for example 2 to 140 hours. After the reaction is complete, any precipitate which has separated out is filtered off, it being possible for the filter medium to consist for example of commercially available filter paper, and washed with the appropriate solvent, and the remaining solid is dried in vacuo, or the reaction mixture is freed of solvent in vacuo. The remaining crude product is purified by recrystallization from a suitable solvent, for example ethanol, or by column or flash chromatography on silica gel or alumina.

A mixture of methanol and dichloromethane for example is used as mobile phase.

Alternatively, if the product is to be a derivative of compound 10 shown in scheme 2, the reaction product 4 after completion of the basic reaction can be reacted with an appropriate nitrile and, where appropriate, a suitable base, preferably sodium amide or sodium hexamethyldisilazide, or a suitable catalyst, for example aluminium trichloride, trimethylaluminium, glacial acetic acid or sulphuric acid, in a suitable inert solvent such as, for example, tetrahydrofuran, toluene or ethanol, or without solvent. The reaction mixture is left to react in a temperature range between 0 and 200° C. for some time, for example 30 minutes to 24 hours. After the reaction is complete, any precipitate which has separated out is filtered off, it being possible for the filter medium to consist for example of commercially available filter paper, and washed with the appropriate solvent, and the remaining solid is dried in vacuo, or the reaction mixture is freed of solvent in vacuo. The remaining crude product is purified by recrystallization from a suitable solvent, for example ethanol, or by column or flash chromatography on silica gel or alumina. A mixture of methanol and dichloromethane for example is used as mobile phase.

Under some of the reaction conditions mentioned, OH, SH and NH$_2$ groups may possibly undergo unwanted side reactions. It is therefore preferred for them to be provided with protective groups, or be replaced by NO$_2$ in the case of NH$_2$, for the protective group subsequently to be eliminated or the NO$_2$ group to be reduced. Thus, in a modification of the process described above, at least one OH group in the starting compounds can be replaced for example by a benzyloxy group and/or at least one SH group can be replaced for example by an S-benzyl group and/or at least one NH$_2$ group can be replaced by an NO$_2$ group. It is subsequently possible to eliminate at least one—preferably all—benzyloxy group(s) for example with hydrogen and palladium on carbon and/or at least one—preferably all—S-benzyl group(s) for example with sodium in ammonia and/or to reduce at least one—preferably all—NO$_2$ group(s) for example with hydrogen and Raney nickel to NH$_2$.

Carboxylic ester and carboxamide groups may possibly undergo unwanted side reactions under some of the reaction conditions mentioned. It is therefore preferred to prepare carboxylic ester and carboxamide groups from process products which contain at least one OH and/or at least one NH$_2$ and/or at least one COOH group. In a modification of the process described above, process products having at least one OH group and/or having at least one NH$_2$ group can be converted by reaction with an activated carboxyl group, for example a carbonyl chloride group, into carboxylic ester or carboxamide groups. In a modification of the process described above, process products having at least one COOH group can be converted by reaction with an activator such as, for example, thionyl chloride or carbonyldiimidazole and subsequent reaction with a suitable alcohol or amine into carboxylic ester or carboxamide groups.

The pyrido[2,3-b]pyrazine derivatives of the invention of the general Formula I are suitable as active ingredients in medicaments, in particular for malignant and other disorders based on pathological cell proliferations, such as, for example, restenosis, psoriasis, arteriosclerosis and cirrhosis of the liver for the treatment of humans, mammals and poultry. Mammals may be domestic animals such as horses, cows, dogs, cats, rabbits, sheep and the like.

The medicinal effect of the pyrido[2,3-b]pyrazine derivatives of the invention may be based for example on inhibition of signal transduction through interaction with receptor tyrosine kinases and with cytoplasmic tyrosine and serine/threonine kinases. In addition, other known and unknown mechanisms of action for controlling malignant processes are also conceivable.

A further aspect of the invention provides a method for controlling tumours in humans and in mammals, which is characterized in that at least one pyrido[2,3-b]pyrazine derivative of the general Formula I is administered to a human or a mammal in an amount effective for tumour treatment. The therapeutically effective dose of the particular pyrido[2,3-b]pyrazine derivative of the invention to be administered for the treatment depends inter alia on the nature and stage of the oncosis, the age and sex of the patient, the mode of administration and the duration of treatment. The medicaments of the invention may be administered as liquid, semisolid and solid pharmaceutical forms. This takes place in the manner suitable in each case in the form of aerosols, powders, dusting powders and epipastics, tablets, coated tablets, emulsions, foams, solutions, suspensions, gels, ointments, pastes, pills, pastilles, capsules or suppositories.

The pharmaceutical form comprises besides at least one ingredient of the invention, depending on the pharmaceutical form employed, where appropriate excipients such as, inter alia, solvents, solution promoters, solubilizers, emulsifiers, wetting agents, antifoams, gelling agents, thickeners, film formers, binders, buffers, salt formers, desiccants, flow regulators, fillers, preservatives, antioxidants, colours, mould release agents, lubricants, disintegrants, and masking tastes and odours. The selection of the excipients, and the amounts thereof to be employed, depends on the chosen pharmaceutical form and is based on the formulas known to the skilled person.

The medicaments of the invention can be administered in a suitable dosage form to the skin, epicutaneously as solution, suspension, emulsion, foam, ointment, paste or plaster; via the oral and lingual mucosa, buccally, lingually or sublingually as tablet, pastille, coated tablets, linctus or gargle; via the gastric and intestinal mucosa, enterally as tablet, coated tablets, capsule, solution, suspension or emulsion; via the rectal mucosa, rectally as suppository, rectal capsule or ointment; via the nasal mucosa, nasally as drops, ointments or spray; via the bronchial and alveolar epithelium, by the pulmonary route or by inhalation as aerosol or inhalant; via the conjunctiva, conjunctivally as eye drops, eye ointment, eye tablets, lamellae or eye lotion; via the mucosa of the genital organs, intravaginally as vaginal suppositories, ointments and douche, by the intrauterine route as uterine pessary; via the urinary tract, intraurethrally as irrigation, ointment or bougie; into an artery, arterially as injection; into a vein, intravenously as injection or infusion; into the skin, intracutaneously as injection or implant; under the skin, subcutaneously as injection or implant; into the muscle, intramuscularly as injection or implant; into the abdominal cavity, intraperitoneally as injection or infusion.

The medicinal effect of the compounds of the invention of the general structure I can be prolonged by suitable measures in the light of practical therapeutic requirements. This aim can be achieved by chemical and/or pharmaceutical means. Examples of the achievement of a prolongation of the effect are the use of implants and liposomes, the formation of salts and complexes of low solubility, or the use of crystal suspensions.

Particularly preferred medicaments in this connection are those which comprise at least one compound from the following group of pyrido[2,3-b]pyrazine derivatives of the general structure I and which may be in the form of their free base or else as pharmaceutically acceptable salts of physiologically tolerated acids:

1-allyl-3-(3-phenylpyrido[2,3-b]pyrazin-6-yl)thiourea (Example 1)

1-allyl-3-(3-naphthalen-2-ylpyrido[2,3-b]pyrazin-6-yl)thiourea (Example 2)

1-allyl-3-[3-(4-methoxyphenyl)pyrido[2,3-b]pyrazin-6-yl]thiourea (Example 3)

1-allyl-3-[3-(4-hydroxyphenyl)pyrido[2,3-b]pyrazin-6-yl]thiourea hydrochloride (Example 4)

1-(2-methylallyl)-3-(3-phenylpyrido[2,3-b]pyrazin-6-yl)thiourea (Example 5)

1-(2-methylallyl)-3-(3-naphthalen-2-ylpyrido[2,3-b]pyrazin-6-yl)thiourea (Example 6)

1-[3-(4-methoxyphenyl)pyrido[2,3-b]pyrazin-6-yl)-3-(2-methylallyl)thiourea (Example 7)

1-(3-naphthalen-2-ylpyrido[2,3-b]pyrazin-6-yl)-3-(4-nitrophenyl)thiourea (Example 8)

1-[3-(4-methoxyphenyl)pyrido[2,3-b]pyrazin-6-yl]-3-(4-nitrophenyl)thiourea (Example 9)

1-tert-butyl-3-(3-phenylpyrido[2,3-b]pyrazin-6-yl)thiourea (Example 10)

1-cyclopropyl-3-(3-phenylpyrido[2,3-b]pyrazin-6-yl)thiourea (Example 11)
1-methyl-3-(3-phenylpyrido[2,3-b]pyrazin-6-yl)thiourea (Example 12)
1-benzyl-3-(3-phenylpyrido[2,3-b]pyrazin-6-yl)thiourea (Example 13)
1-(4-fluorophenyl)-3-(3-phenylpyrido[2,3-b]pyrazin-6-yl)thiourea (Example 14)
1-(3-phenylpyrido[2,3-b]pyrazin-6-yl)-3-p-tolylurea (Example 15)
1-(4-chloro-3-trifluoromethylphenyl)-3-(3-phenylpyrido[2,3-b]pyrazin-6-yl)urea (Example 16)
1-(2-morpholin-4-ylethyl)-3-(3-phenylpyrido[2,3-b]pyrazin-6-yl)urea (Example 17)

EXEMPLARY EMBODIMENTS

The following compounds, which are evident from the statement of the respective chemical name from the survey hereinafter, were synthesized in accordance with the general methods for stages 1-3 on which the synthesis schemes 1 and 2 are based. In addition, their NMR spectroscopic data and melting points are appended. The structure of these compounds are evident from the general Formula II and the substituents R1, R2, X and Y in Table 1 which follows.

The chemicals and solvents employed were obtained commercially from conventional suppliers (Acros, Aldrich, Fluka, Lancaster, Maybridge, Merck, Sigma, TCI, etc.) or synthesized.

The invention is to be explained in more detail by means of the following examples without being restricted thereto.

EXAMPLE 1

Preparation of 3-phenylpyrido[2,3-b]pyrazin-6-ylamine (reaction shown in scheme 1, 1st and 2nd stage)

A solution of 1.22 g of 2,6-diamino-3-nitropyridine (7.92 mmol) in 210 ml of ethanol is hydrogenated with Raney nickel as catalyst at 50° C. and 5 bar. After the hydrogenation is complete, the catalyst is filtered off with suction through a glass fibre filter. Before the filtration, 1.68 g of phenylglyoxal hydrate (11.03 mmol) are introduced into 50 ml of ethanol in the receiver. The catalyst is then filtered off under nitrogen as protective gas, and the hydrogenation solution is sucked directly into the reaction flask. The greenish blue reaction mixture is heated under reflux under nitrogen for 30 min. The mixture is allowed to cool, and the solvent is removed in vacuo. A dark brown solid is finally obtained. Purification by column chromatography on silica gel (mobile phase dichloromethane/methanol mixture) affords a pale yellow crystalline solid.

Preparation of 1-allyl-3-(3-phenylpyrido[2,3-b]pyrazin-6-yl)thiourea (reaction shown in scheme 2, 3rd stage)

0.246 g of sodium hydride (6.14 mmol) is introduced into 5 ml of anhydrous dimethylformamide under nitrogen as protective gas. The mixture is cooled to 0° C. in an ice bath. 1.05 g of 3-phenylpyrido[2,3-b]pyrazin-6-ylamine (4.72 mmol) are dissolved in 5 ml of anhydrous dimethylformamide and added dropwise. The cooling bath is removed, and the mixture is left to stir at RT for 30 minutes. The mixture is then cooled to 0° C. again in the ice bath, and 0.469 g of allyl isothiocyanate (4.72 mmol), dissolved in 4 ml of anhydrous dimethylformamide, is added dropwise. After the addition is complete, the cooling bath is removed, and the mixture is then left to stir at room temperature for 1.5 hours. For working up, the mixture is poured into about 250 ml of distilled water, and the precipitated orange solid is filtered off with suction. Purification by column chromatography several times (mobile phases dichloromethane/methanol mixtures) and subsequent purification by preparative HPLC afford a yellow solid.

Melting point: 239-240° C. (decomp.) $^1$H-NMR ($d_6$-DMSO): δ=4.40 (m, 2H), 5.30 (d, 1H), 5.60 (d, 1H), 6.07-6.17 (m, 1H), 7.55-7.70 (m, 4H), 8.35 (d, 2H), 8.45 (d, 1H), 9.50 (s, 1H), 11.35 (s, 1H), 12.55 (m, 1H).

The following examples were synthesized as in Example 1:

EXAMPLE 2

1-Allyl-3-(3-naphthalen-2-ylpyrido[2,3-b]pyrazin-6-yl)thiourea m.p.: 242-243° C. (decomp.) $^1$H-NMR ($d_6$-DMSO): δ=4.42 (m, 2H), 5.37 (d, 1H), 5.65 (d, 1H), 6.07-6.19 (m, 1H), 7.57-7.68 (m, 3H), 7.97-8.05 (m, 1H), 8.07-8.19 (m, 2H), 8.40-8.52 (m, 2H), 8.99 (s, 1H), 9.70 (s, 1H), 11.36 (s, 1H), 12.56 (t, 1H).

EXAMPLE 3

1-Allyl-3-[3-(4-methoxyphenyl)pyrido[2,3-b]pyrazin-6-yl]thiourea m.p.: 240-241° C. (decomp.) $^1$H-NMR ($d_6$-DMSO): δ=3.87 (s, 3H), 4.36-4.42 (m, 2H), 5.32 (d, 1H), 5.60 (d, 1H), 6.06-6.16 (m, 1H), 7.16 (d, 2H), 7.60 (d, 1H), 8.32 (d, 2H), 8.42 (d, 1H), 9.56 (s, 1H), 11.29 (s, 1H), 12.56 (m, 1H).

EXAMPLE 4

1-Allyl-3-[3-(4-hydroxyphenyl)pyrido[2,3-b]pyrazin-6-yl]thiourea hydrochloride m.p.: 160-161° C. (decomp.) $^1$H-NMR ($d_6$-DMSO): δ=4.36-4.43 (m, 2H), 5.31 (d, 1H), 5.59 (d, 1H), 6.05-6.16 (m, 1H), 6.97 (d, 2H), 7.57 (d, 1H), 8.20 (d, 2H), 8.40 (d, 1H), 9.41 (s, 1H), 10.17 (bs, 1H), 11.24 (s, 1H), 12.56 (m, 1H).

EXAMPLE 5

1-(2-Methylallyl)-3-(3-phenylpyrido[2,3-b]pyrazin-6-yl)thiourea m.p.: 225-226° C. (decomp.) $^1$H-NMR ($d_6$-DMSO): δ=1.90 (s, 3H), 4.30-4.35 (m, 2H), 5.01 (s, 1H), 5.22 (s, 1H), 7.55-7.80 (m, 4H), 8.30-8.38 (m, 2H), 8.45 (d, 1H), 9.52 (s, 1H), 11.32 (s, 1H), 12.65 (m, 1H).

EXAMPLE 6

1-(2-Methylallyl)-3-(3-naphthalen-2-ylpyrido[2,3-b]pyrazin-6-yl)thiourea m.p.: 239-240° C. (decomp.) $^1$H-NMR ($d_6$-DMSO): δ=1.94 (s, 3H), 4.32 (m, 2H), 5.07 (s, 1H), 5.28 (s, 1H), 7.60-7.69 (m, 3H), 8.00-8.5 (m, 1H), 8.07-8.12 (m, 1H), 8.14 (d, 1H), 8.42-8.51 (m, 2H), 8.98 (s, 1H), 9.68 (s, 1H), 11.32 (s, 1H), 12.78 (m, 1H).

EXAMPLE 7

1-[3-(4-Methoxyphenyl)pyrido[2,3-b]pyrazin-6-yl]-3-(2-methylallyl)thiourea m.p.: 251-252° C. (decomp.) $^1$H-NMR (d$_6$-DMSO): δ=1.92 (s, 3H), 3.85 (s, 3H), 4.27 4.35 (m, 2H), 5.02 (s, 1H), 5.24 (s, 1H), 7.15 (d, 2H), 7.58 (d, 1H), 8.31 (d, 2H), 8.41 (d, 1H), 9.46 (s, 1H), 11.29 (s, 1H), 12.68 (m, 1H).

EXAMPLE 8

1-(3-Naphthalen-2-ylpyrido[2,3-b]pyrazin-6-yl)-3-(4-nitrophenyl)thiourea m.p.: 260-261° C. (decomp.) $^1$H-NMR (d$_6$-DMSO): δ=7.61-7.68 (m, 3H), 7.72 (d, 2H), 7.75 (d, 1H), 8.01-8.06 (m, 1H), 8.16 (m, 2H), 8.26 (d, 2H), 8.53 (d, 1H), 8.58 (d, 1H), 9.04 (s, 1H), 9.62 (s, 1H), 9.76 (s, 1H), 11.81 (s, 1H).

EXAMPLE 9

1-[3-(4-Methoxyphenyl)pyrido[2,3-b]pyrazin-6-yl]-3-(4-nitrophenyl)thiourea m.p.: 250-251° C. (decomp.) $^1$H-NMR (d$_6$-DMSO): δ=3.85 (s, 3H), 7.17 (d, 2H), 7.71 (d, 2H), 8.21 (d, 2H), 8.22-8.27 (m, 1H), 8.36-8.42 (m, 3H), 9.53 (s, 1H), 9.65 (s, 1H), 11.77 (s, 1H).

EXAMPLE 10

1-tert-Butyl-3-(3-phenylpyrido[2,3-b]pyrazin-6-yl)thiourea m.p.: 227° C. (decomp.) $^1$H-NMR (d$_6$-DMSO): δ=1.65 (s, 9H), 7.53-7.69 (m, 4H), 8.34 (d, 2H), 8.41 (d, 1H), 9.51 (s, 1H), 10.98 (s, 1H), 12.75 (s, 1H).

EXAMPLE 11

1-Cyclopropyl-3-(3-phenylpyrido[2,3-b]pyrazin-6-yl)thiourea m.p.: 233-234° C. $^1$H-NMR (d$_6$-DMSO): δ=0.70-0.80 (m, 2H), 0.91-1.00 (m, 2H), 3.20-3.28 (m, 1H), 7.51-7.72 (m, 4H), 8.36 (d, 2H), 8.45 (d, 1H), 9.52 (s, 1H), 11.31 (s, 1H), 12.45 (s, 1H).

EXAMPLE 12

1-Methyl-3-(3-phenylpyrido[2,3-b]pyrazin-6-yl)thiourea m.p.: 253-254° C. $^1$H-NMR (d$_6$-DMSO): δ=3.25 (s, 3H), 7.59-7.67 (m, 4H), 8.38 (d, 2H), 8.46 (d, 1H), 9.52 (s, 1H), 11.31 (s, 1H), 12.10 (s, 1H).

EXAMPLE 13

1-Benzyl-3-(3-phenylpyrido[2,3-b]pyrazin-6-yl)thiourea m.p.: 232-233° C. $^1$H-NMR (d$_6$-DMSO): δ=4.96 (m, 2H), 7.37-7.48 (m, 3H), 7.54-7.67 (m, 6H), 8.32 (d, 2H), 8.47 (d, 1H), 9.52 (s, 1H), 11.43 (s, 1H), 12.91 (s, 1H).

EXAMPLE 14

1-(4-Fluorophenyl)-3-(3-phenylpyrido[2,3-b]pyrazin-6-yl)thiourea m.p.: 225-226° C. $^1$H-NMR (d$_6$-DMSO): δ=7.33 (m, 2H), 7.57-7.65 (m, 3H), 7.70-7.81 (m, 3H), 8.34 (d, 2H), 8.54 (d, 1H), 9.57 (s, 1H), 11.62 (s, 1H).

EXAMPLE 15

1-(3-Phenylpyrido[2,3-b]pyrazin-6-yl)-3-p-tolylurea m.p.: 298-299° C. $^1$H-NMR (d$_6$-DMSO): δ=2.29 (s, 3H), 7.20 (d, 2H), 7.52 (d, 2H), 7.59-7.67 (m, 3H), 7.80 (d, 1H), 8.38 (d, 2H), 8.44 (d, 1H), 9.59 (s, 1H), 10.36 (s, 1H), 11.46 (s, 1H).

EXAMPLE 16

1-(4-Chloro-3-trifluoromethylphenyl)-3-(3-phenylpyrido[2,3-b]pyrazin-6-yl)urea m.p.: 250° C. $^1$H-NMR (d$_6$-DMSO): δ=7.58-7.67 (m, 3H), 7.74 (d, 1H), 7.80 (d, 1H), 7.87 (d, 1H), 8.21 (s, 1H), 8.39 (d, 2H), 8.48 (d, 1H), 9.53 (s, 1H), 10.55 (s, 1H), 11.82 (s, 1H).

EXAMPLE 17

1-(2-Morpholin-4-ylethyl)-3-(3-phenylpyrido[2,3-b]pyrazin-6-yl)urea m.p.: 226° C. $^1$H-NMR (d$_6$-DMSO): δ=2.45-2.67 (m, 6H), 3.40-3.48 (m, 2H), 3.60-3.69 (m, 4H), 7.55-7.70 (m, 4H), 8.30-8.40 (m, 3H), 9.29 (s, 11H), 9.42 (s, 1H), 10.18 (s, 1H).

TABLE 1

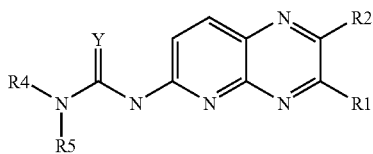

II

| Ex. | Y | R1 | R2 | R4 | R5 | NMR | Salt |
|---|---|---|---|---|---|---|---|
| 1 | S | Ph | H | —CH$_2$CH=CH$_2$ | H | $^1$H | |
| 2 | S | 2-naphthyl | H | —CH$_2$CH=CH$_2$ | H | $^1$H | |
| 3 | S | 4-MeO—Ph | H | —CH$_2$CH=CH$_2$ | H | $^1$H | |
| 4 | S | 4-HO—Ph | H | —CH$_2$CH=CH$_2$ | H | $^1$H | HCl |
| 5 | S | Ph | H | —CH$_2$C(CH$_3$)=CH$_2$ | H | $^1$H | |
| 6 | S | 2-naphthyl | H | —CH$_2$C(CH$_3$)=CH$_2$ | H | $^1$H | |
| 7 | S | 4-MeO—Ph | H | —CH$_2$C(CH$_3$)=CH$_2$ | H | $^1$H | |
| 8 | S | 2-naphthyl | H | —Ph-p-NO$_2$ | H | $^1$H | |
| 9 | S | 4-MeO—Ph | H | —Ph-p-NO$_2$ | H | $^1$H | |
| 10 | S | Ph | H | —C(CH$_3$)$_3$ | H | $^1$H | |
| 11 | S | Ph | H | -cyclopropyl | H | $^1$H | |
| 12 | S | Ph | H | —CH$_3$ | H | $^1$H | |
| 13 | S | Ph | H | -benzyl | H | $^1$H | |
| 14 | S | Ph | H | —Ph-p-F | H | $^1$H | |
| 15 | O | Ph | H | -p-tolyl | H | $^1$H | |
| 16 | O | Ph | H | —Ph-p-Cl-m-CF$_3$ | H | $^1$H | |
| 17 | O | Ph | H | —CH$_2$CH$_2$-morpholin-4-yl | H | $^1$H | |

Biological Effects of the Compounds of the Invention

The inhibitory effect on the following human serine/threonine and tyrosine kinases of the compounds of the invention was tested in conventional kinase assays: PKB/Akt1, c-Raf, B-Raf, Mek, PDGFRbeta, Flt-3, c-Kit, c-Abl, KDR, FGFR1 and IGF1R. Both the full-length kinases and truncated fragments—but at least the cytoplasmic, constitutively active kinase domains—were employed. The kinases were prepared as recombinant fusion proteins with GST (glutathion S-transferase) or HIS Tag in Sf9 cell culture. Depending on the substrate type, the various kinase reactions were carried out in sandwich ELISA formats or by means of a simple substrate adsorption assay on 96-well Flashplates (Perkin Elmer).

The testing on substances on the Raf-Mek-Erk cascade is described in detail below. Selected test results for the Raf and Mek inhibitors are then listed.

Procedure: Raf-Mek-Erk ELISA

Potential inhibitors were firstly investigated at a concentration of 20 µg/ml in initial single-dose determinations on 96-well microtiter plates (MTPs). Substances with >70% inhibition were employed for dose-response studies.

Reconstitution of the Raf-Mek-Erk cascade was quantified with the aid of a cell-free ELISA. The following recombinant prepared kinase proteins were used: 1.) constitutively active GST-c-Raf-DD from Sf9 cells, 2.) inactive GST-Mek1 from E. coli and 3.) inactive His-Erk2 from E. coli.

A typical kinase assay was carried out in a final volume of 50 µl with in each case 20-150 ng of Raf, Mek, Erk kinase protein, 1 mM ATP, 10 mM $MgCl_2$, 150 mM NaCl, 25 mM beta-glycerophosphate, 25 mM Hepes pH 7.5. Before the kinase reaction, the test substances were each preincubated singly with each of the three kinase proteins at room temperature for 30 minutes. For the kinase reaction, the kinases preincubated with test substance were combined and incubated at 26° C. for 30 minutes. The reaction was stopped by a final concentration of 2% SDS and 10 minutes at 50° C. in a heating block.

For the immunodetection, the reaction mixtures were transferred to 96-well MTPs coated with anti-Erk Ab(K-23, Santa Cruz Biotechnology, incubated at room temperature for 60 minutes and washed 3× with TBST. Anti-phospho-Erk Ab (#9106, New England Biolabs) 1:500 in 50 µl of TBST/1% BSA, was added and incubated at 4° C. overnight. After the MTPs had been washed 3× with TBST, secondary anti-mouse IgG$^{POD}$ conjugate (#NA931, Pharmacia) 1:2500 was added, incubated at room temperature for 1 h and again washed 3× with TBST. For colorimetric detection of the kinase reaction, 50 µl of OPD (o-phenyldiamine dihydrochloride) chromogen buffer were pipetted into each of the wells and incubated at 37° C. for 30 minutes. The colour reaction was then determined in an ELISA reader at 492 nm.

The experimental determination of dose-response plots took place using the same experimental design with 10 semilogarithmically graded concentrations from 31.6 pM-100 µM. The $IC_{50}$ values were calculated in GraphPad-Prism.

The compounds of the invention show effective inhibition of Erk phosphorylation with $IC_{50}$ values ranging to 400 nM (see exemplary embodiments 4 and 12).

| Exemplary embodiment | $IC_{50}$ (µM) |
|---|---|
| 1 | ca. 1.0/3.0 |
| 2 | 16 |
| 3 | ca. 1.0 |
| 4 | 0.4 |
| 5 | ca. 1.0 |
| 6 | ca. 100 |
| 7 | 43 |
| 8 | >100 |
| 9 | >100 |
| 10 | >100 |
| 11 | 0.9 |
| 12 | 0.4 |
| 13 | >100 |
| 14 | ca. 50 |
| 15 | >100 |
| 16 | >100 |
| 17 | 15 |

We claim:

1. Novel pyrido[2,3-b]pyrazine derivative compound of general Formula I

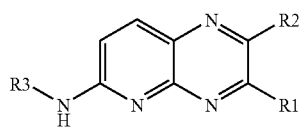

in which the substituents R1-R3 have the following meaning:

R1 and R2 may be independently of one another:
(i) hydrogen,
(ii) hydroxyl,
(iii) alkyl, alkenyl or akynyl, where the alkyl radical is saturated and having 1 to 8 C atoms, the alkenyl radical has 2 to 8 C atoms, the alknyl radical has 2 to 8 C atoms,
(iv) unsubstituted or substituted aryl, where the aryl radical may have one or more identical or different F, Cl, Br, I, $CF_3$, CN, $NH_2$, NH-alkyl, NH-cycloalkyl, NH-heterocyclyl, NH-aryl, NH-hetero-aryl, NH-alkyl-cycloalkyl, NH-alkyl-heterocyclyl, NH-alkyl-aryl, NH-alkyl-heteroaryl, NH-alkyl-$NH_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, $NHSO_2$-alkyl, $NHSO_2$-aryl, $NHSO_2$-heteroaryl, $NO_2$, SH, S-alkyl, S-aryl, S-heteroaryl, OH, $OCF_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, OC(O)-alkyl, OC(O)-cycloalkyl, OC(O)-heterocyclyl, OC(O)-aryl, OC(O)-heteroaryl, $OSO_2$-alkyl, $OSO_2$-aryl, $OSO_2$-heteroaryl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkylcycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, $SO_2$-alkyl, $SO_2$-aryl, $SO_2NH_2$, $SO_2$NH-alkyl, $SO_2$NH-aryl, $SO_2$NH-heteroaryl, $SO_3H$, $SO_2$O-alkyl, $SO_2$O-aryl, alkyl, cycloalkyl, heterocyclyl, aryl, heteroaryl, NH-alkenyl-cycloalkenyl, NH-alkenyl-heterocyclyl, NH-alkenyl-aryl, NH-alkenyl-heteroaryl, NH-alkenyl-NH$_2$, NH-alkenyl-OH, N(alkenyl)$_2$, NHC(O)-alkenyl, NHC(O)-cycloalkenyl, NHSO$_2$-alkenyl, S-alkenyl, O-alkenyl, O-cycloalkenyl, O-alkenyl-cycloalkenyl, O-alkenylheterocyclyl, O-alkenyl-aryl, O-alkenyl-heteroaryl, O-alkenyl-OH, OC(O)-alkenyl, OC(O)-cycloalkenyl, OSO$_2$-alkenyl, CO$_2$-alkenyl, CO$_2$-cycloalkenyl, CO$_2$-alkylcycloalkenyl, CO$_2$-alkenyl-heterocyclyl, CO$_2$-alkenyl-aryl, CO$_2$-alkenyl-heteroaryl, C(O)NH-alkenyl, C(O)NH-cycloalkenyl, C(O)NH-alkenyl-cycloalkenyl, C(O)NH-alkenyl-heterocyclyl, C(O)NH-alkenyl-aryl, C(O)NH-alkenyl-heteroaryl, C(O)N(alkenyl)$_2$, SO$_2$-alkenyl, SO$_2$NH-alkenyl, SO$_2$O-alkenyl, alkenyl, cycloalkenyl, NH-alkyl-cycloalkynyl, NH-alkynyl-heterocyclyl, NH-alkynyl-aryl, NH-alkynyl-heteroaryl, NH-alkynyl-NH$_2$, NH-alkynyl-OH, N(alkynyl)$_2$, NHC(O)-alkynyl, NHC(O)-cycloalkynyl, NHSO$_2$-alkynyl, S-alkynyl, O-alkynyl, O-cycloalkynyl, O-alkynyl-cycloalkynyl, O-alkynyl-heterocyclyl, O-alkynyl-aryl, O-alkynyl-heteroaryl, O-alkynyl-ON, OC(O)-alkynyl, OC(O)-cycloalkynyl, OSO$_2$-alkynyl, CO$_2$-alkynyl, CO$_2$-cycloalkynyl, CO$_2$-alkylcycloalkynyl, CO$_2$-alkynyl-heterocyclyl, CO$_2$-alkynyl-aryl, CO$_2$-alkynyl-heteroaryl, C(O)NH-alkynyl, C(O)NH-cycloalkynyl, C(O)NH-alkynyl-cycloalkyl, C(O)NH-alkynyl-heterocyclyl, C(O)NH-alkynyl-aryl, C(O)NH-alkynyl-heteroaryl, C(O)N(alkynyl)$_2$, SO$_2$-alkynyl, SO$_2$NH-alkynyl, SO$_2$O-alkynyl, alkynyl, or cycloalkynyl substituents, and the alkyl, cycloalkyl, heterocylyl, aryl, heteroaryl, alkyl-cycloalkyl, alkyl-heterocyclyl, alkyl-aryl, alkylheteroaryl, alkenyl, cycloalkenyl, alkenyl-cycloalkenyl, alkenyl-heterocyclyl, alkenyl-aryl, alkenylheteroaryl, alkynyl, cycloalkynyl, alkynyl-cycloalkynyl, alkynyl-heterocyclyl, alkynyl-aryl, alkylheteroaryl substituents may in turn themselves be substituted, (v) unsubstituted or substituted heteroaryl, where the heteroaryl radical may have one or more identical or different F, Cl, Br, I, CF$_3$, CN, NH$_2$, NH-alkyl, NH-cycloalkyl, NH-heterocyclyl, NH-aryl, NH-heteroaryl, N(alkyl)$_2$, NHC(O)-alkyl, NHC(O)-cycloalkyl, NHC(O)-heterocyclyl, NHC(O)-aryl, NHC(O)-heteroaryl, NHSO2-alkyl, NHSO$_2$-aryl, NHSO$_2$-heteroaryl, NO$_2$, SH, S-alkyl, S-aryl, OH, OCF$_3$, O-alkyl, O-cycloalkyl, O-aryl, O-heteroaryl, OC(O)-alkyl, OC(O)-cycloalkyl, OC(O)-heterocyclyl, OC(O)-aryl, OC(O)-heteroaryl, OSO$_2$-alkyl, OSO$_2$-cycloalkyl, OSO$_2$-aryl, OSO$_2$-heteroaryl, C(O)-alkyl, C(O)-aryl, CO$_2$H, CO$_2$-alkyl, CO$_2$-cycloalkyl, CO$_2$-heterocyclyl, CO$_2$-aryl, CO$_2$-heteroaryl, C(O)—NH$_2$, C(O)NH-alkyl, C(O)NH-cycloalkyl, C(O)NH-hetero-cyclyl, C(O)NH-aryl, C(O)NH-heteroaryl, N(alkyl)$_2$, SO$_2$NH$_2$, SO$_2$NH-alkyl, SO$_2$NH-aryl, SO$_3$H, SO$_2$O-alkyl, SO$_2$O-aryl, alkyl, cycloalkyl, heterocyclyl, aryl, heteroaryl, NH-alkenyl, NH-cycloalkenyl, N(alkenyl)$_2$, NHC(O)-alkenyl, NHC(O)-cycloalkenyl, NHSO$_2$-alkenyl, S-alkenyl, O-alkenyl, O-cycloalkenyl, OC(O)-alkenyl, OC(O)-cycloalkenyl, OSO$_2$-alkenyl, OSO$_2$-cycloalkenyl, C(O)-alkenyl, CO$_2$-alkenyl, CO$_2$-cycloalkenyl, C(O)NH-alkenyl, C(O)NH-cycloalkenyl, N(alkenyl)$_2$, SO$_2$O-alkenyl, alkenyl, cycloalkenyl, NH-alkynyl, NH-cycloalkynyl, N(alkynyl)$_2$, NHC(O)-alkynyl, NHC(O)-cycloalkynyl, NHSO$_2$-alkynyl, S-alkynyl, O-alkynyl, O-cycloalkynyl, OC(O)-alkynyl, OC(O)-cycloalkynyl, OSO$_2$-alkynyl, OSO$_2$-cycloalkynyl, C(O)-alkynyl, CO$_2$-alkynyl, CO$_2$-cycloalkynyl, C(O)NH-alkynyl, C(O)NH-cycloalkynyl, N(alkynyl)$_2$, SO$_2$O-alkynyl, alkynyl, or cycloalkynyl substituents, and the alkyl, cycloalkyl, heterocyclyl, aryl, heteroaryl, alkenyl, cycloalkenyl, alkynyl, and cycloalkynyl substituents may in turn themselves be substituted R3 is A, B, or C, where:

(A) is —C(Y)NR4R5, where Y is O, or S and R4 and R5 are independently of one another (i) hydrogen, (ii) unsubstituted or substituted alkyl, alkenyl or alkynyl, where the alkyl, the alkenyl or the alkynyl radical may have one or more identical or different F, Cl, Br, I, CF$_3$, CN, NH$_2$, NH-alkyl, NH-cycloalkyl, NH-heterocyclyl, NH-aryl, NH-heteroaryl, NH-alkyl-aryl, NH-alkyl-heteroaryl, N(alkyl)2, NHC(O)-alkyl, NHC(O)-cycloalkyl, NHC(O)-heterocyclyl, NHC(O)-aryl, NHC(O)-heteroaryl, NHSO$_2$-alkyl, NHSO$_2$-cycloalkyl, NHSO$_2$-aryl, NHSO$_2$-heteroaryl, NO2, SH, S-alkyl, S-cycloalkyl, S-heterocyclyl, S-aryl, S-heteroaryl, OH, OCF$_3$, O-alkyl, O-cycloalkyl, O-heterocyclyl, O-aryl, O-heteroaryl, O-alkyl-cycloalkyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OSO$_2$-alkyl, OSO$_2$-cycloalkyl, OSO$_2$-aryl, CO$_2$-heterocyclyl, C(O)-alkyl, C(O)-aryl, CO$_2$H, CO$_2$-alkyl, CO$_2$-cycloalkyl, (CO$_2$-heterocyclyl, CO$_2$-aryl, CO$_2$-heteroaryl, CO$_2$-alkyl-cycloalkyl, CO$_2$-alkyl-hetero-cyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-hetero-cyclyl, C(O)NH-alkyl-aryl, C(O)NH-alkyl-heteroaryl, C(O)N(alkyl)$_2$, C(O)N(cycloalkyl)$_2$, C(O)N (aryl)$_2$, C(O)N(heteroaryl)$_2$, SO-alkyl, SO-aryl, SO$_2$-alkyl, SO$_2$-aryl, SO$_2$NH$_2$, SO$_3$H, alkyl, cycloalkyl, heterocyclyl, aryl, heteroaryl, NH-alkenyl, NH-cycloalkenyl, NH-alkenyl-aryl, NH-alkenyl-heteroaryl, N(alkenyl)$_2$, NHC(O)-alkenyl, NHC(O)-cycloalkenyl, NHSO$_2$-alkenyl, NHSO$_2$-cycloalkenyl, S-alkenyl, S-cycloalkenyl, O-alkenyl, O-cycloalkenyl, O-alkenyl-cycloalkenyl, O-alkenyl-aryl, O-alkenyl-heteroaryl, OC(O)-alkenyl, OC(O)-cycloalkenyl, OSO$_2$-alkenyl, OSO$_2$-cycloalkenyl, C(O)-alkenyl, CO$_2$-alkenyl, CO$_2$-cycloalkenyl, CO$_2$-alkenyl-cycloalkenyl, CO$_2$-alkenyl-hetero-cyclyl, CO$_2$-alkenyl-aryl, CO$_2$-alkenyl-heteroaryl, C(O)NH-alkenyl, C(O)NH-cycloalkenyl, C(O)NH-alkenyl-cycloalkenyl, C(O)NH-alkenyl-hetero-cyclyl, C(O)NH-alkenyl-aryl, C(O)NH-alkenyl-heteroaryl, C(O)N(alkenyl)$_2$, C(O)N(cycloalkenyl)$_2$, SO$_2$-alkenyl, alkenyl, cycloalkenyl, NH-alkynyl, NH-cycloalkynyl, NH-alkynyl-aryl, NH-alkynyl-heteroaryl, N(alkynyl)$_2$, NHC(O)-alkynyl, NHC(O)-cycloalkynyl, NHSO$_2$-alkynyl, NHSO$_2$-cycloalkynyl, S-alkynyl, S-cycloalkynyl, O-alkynyl, O-cycloalkynyl, O-alkynyl-cycloalkynyl, O-alkynyl-aryl, O-alkynyl-heteroaryl, OC(O)-alkynyl, OC(O)-cycloalkynyl, OSO$_2$-alkynyl, OSO$_2$-cycloalkynyl, C(O)-alkynyl, CO$_2$-alkynyl, CO$_2$-cycloalkynyl, CO$_2$-alkynyl-cycloalkynyl, CO$_2$-alkynyl-hetero-cyclyl, CO$_2$-alkynyl-aryl, CO$_2$-alkynyl-heteroaryl, C(O)NH-alkynyl, C(O)NH-cycloalkynyl, C(O)NH-alkynyl-cycloalkynyl, C(O)NH-alkynyl-hetero-cyclyl, C(O)NH-alkynyl-aryl, C(O)NH-alkynyl-heteroaryl, C(O)N(alkynyl)$_2$, C(O)

N(cycloalkynyl)$_2$, SO$_2$-alkynyl, alkynyl, or cycloalkynyl, substituents, (iii) unsubstituted or substituted cycloalkyl, cycloalkenyl, or cycloalkynyl, where the cycloalkyl, the cycloalkenyl or the cycloalkynyl radical may have one or more identical or different F, Cl, Br, I, NH$_2$, NH-alkyl, NH-cycloalkyl, NH-heterocyclyl, NH-aryl, NH-heteroaryl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHSO$_2$-alkyl, NHSO$_2$-cycloalkyl, NHSO$_2$-aryl, NHSO$_2$-heteroaryl, OH, O-alkyl, O-cycloalkyl, O-heterocyclyl, O-aryl, O-heteroaryl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OSO$_2$-alkyl, OSO$_2$-cycloalkyl, OSO$_2$-aryl, OSO$_2$-heteroaryl, CO2H, CO$_2$-alkyl, CO$_2$-cycloalkyl, CO$_2$-heterocyclyl, CO$_2$-aryl, CO$_2$-heteroaryl, C(O)—NH$_2$, C(O)NH-aryl, C(O)NH-cycloalkyl, C(O)NH-heterocyclyl, C(O)NH-aryl, C(O)NH-heteroaryl, C(O)NH-alkyl-aryl, C(O)NH-alkyl-heteroaryl, C(O)N(alkyl)$_2$, alkyl, aryl, NH-alkenyl, NH-cycloalkenyl, NH-alkenyl-aryl, NH-alkenyl-heteroaryl, N(alkenyl)$_2$, NHC(O)-alkenyl, NHC(O)-cycloalkenyl, NHSO$_2$-alkenyl, NHSO$_2$-cycloalkenyl, O-alkenyl, O-cycloalkenyl, O-alkenyl-aryl, O-alkenyl-heteroaryl, OC(O)-alkenyl, OC(O)-cycloalkenyl, OSO$_2$-alkenyl, OSO$_2$-cycloalkenyl, CO$_2$-alkenyl, CO$_2$-cycloalkenyl, C(O)NH-cycloalkenyl, C(O)NH-alkenyl-aryl, C(O)NH-alkenyl-heteroaryl, C(O)N(alkenyl)$_2$, alkenyl, NH-alkynyl, NH-cycloalkynyl, NH-alkynyl-aryl, NH-alkynyl-heteroaryl, N(alkynyl)$_2$, NHC(O)-alkynyl, NHC(O)-cycloalkynyl, NHSO$_2$-alkynyl, NHSO$_2$-cycloalkynyl, O-alkynyl, O-cycloalkynyl, O-alkynyl-aryl, O-alkynyl-heteroaryl, OC(O)-alkynyl, OC(O)-cycloalkynyl, OSO$_2$-alkynyl, OSO$_2$-cycloalkynyl, CO$_2$-alkynyl, CO$_2$-cycloalkynyl, C(O)NH-cycloalkynyl, C(O)NH-alkynyl-aryl, C(O)NH-alkynyl-heteroaryl, C(O)N(alkynyl)$_2$, or alkynyl substituents, (iv) unsubstituted or substituted heterocylyl, where the heterocyclyl radical may have one or more identical or different OH, O-alkyl, O-aryl, NH-alkyl, NH-aryl, alkyl, alkyl-aryl, aryl, O-alkenyl, NH-alkenyl, alkenyl, alkenyl-aryl, O-alkynyl, NH-alkynyl, alkynyl, or alkynyl-aryl substituents, (v) unsubstituted or substituted aryl, where the aryl radical may have one or more identical or different F, Cl, Br, I, CF$_3$, CN, NH$_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-NH$_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHSO$_2$-alkyl, NHSO$_2$-aryl, NHSO$_2$-heteroaryl, NO$_2$, SH, S-alkyl, S-cycloalkyl, S-heterocyclyl, S-aryl, S-heteroaryl, OH, OCF$_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, OC(O)-alkyl, OC(O)-cycloalkyl, OC(O)-hetero-cyclyl, OC(O)-aryl, OC(O)-heteroaryl, OSO$_2$-alkyl, OSO$_2$-cycloalkyl, OSO$_2$-aryl, OSO$_2$-heteroaryl, C(O)-alkyl, C(O)-aryl, C(O)-heteroaryl, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkyl-hetero-cyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, SO-$_2$-alkyl, SO$_2$-aryl, SO$_2$NH$_2$, SO$_2$NH-alkyl, SO$_2$NH-aryl, SO$_2$NH-heteroaryl, SO$_3$H, SO$_2$O-alkyl, SO$_2$O-aryl, SO$_2$O-heteroaryl, alkyl, cycloalkyl, heterocyclyl, aryl, heteroaryl, NH-alkenyl-cycloalkenyl, NH-alkenyl-heterocyclyl, NH-alkenyl-aryl, NH-alkenyl-heteroaryl, NH-alkenyl-NH$_2$, NH-alkenyl-OH, N(alkenyl)$_2$, NHC(O)-alkenyl, NHC(O)-cycloalkenyl, NHSO$_2$-alkenyl, S-alkenyl, S-cycloalkenyl, O-alkenyl, O-cycloalkenyl, O-alkenyl-cycloalkenyl, O-alkenyl-heterocyclyl, O-alkenyl-aryl, O-alkenyl-heteroaryl, O-alkenyl-OH, OC(O)-alkenyl, OC(O)-cycloalkenyl, OSO$_2$-alkenyl, OSO$_2$-cycloalkenyl, C(O)-alkenyl, CO$_2$-alkenyl, CO$_2$-cycloalkenyl, CO$_2$-alkenyl-cycloalkenyl, CO$_2$-alkenyl-hetero-cyclyl, CO$_2$-alkenyl-aryl, CO$_2$-alkenyl-heteroaryl, C(O)NH-alkenyl, C(O)NH-cycloalkenyl, C(O)NH-alkenyl-cycloalkenyl, C(O)NH-alkenyl-heterocyclyl, C(O)NH-alkenyl-aryl, C(O)NH-alkenyl-heteroaryl, C(O)N(alkenyl)$_2$, C(O)N(cycloalkenyl)$_2$, SO-alkenyl, SO$_2$-alkenyl, SO$_2$NH-alkenyl, SO$_2$O-alkenyl, SO$_2$O-aryl, alkenyl, cycloalkenyl, NH-alkynyl-cycloalkynyl, NH-alkynyl-heterocyclyl, NH-alkynyl-aryl, NH-alkynyl-heteroaryl, NH-alkynyl-NH$_2$, NH-alkynyl-OH, N(alkynyl)$_2$, NHC(O)-alkynyl, NHC(O)-cycloalkynyl, NHSO$_2$-alkynyl, S-alkynyl, S-cycloalkynyl, O-alkynyl, O-cycloalkynyl, O-alkynyl-cycloalkynyl, O-alkynyl-heterocyclyl, O-alkynyl-aryl, O-alkynyl-heteroaryl, O-alkynyl-OH, OC(O)-alkynyl, OC(O)-cycloalkynyl, OSO$_2$-alkynyl, OSO$_2$-cycloalkynyl, C(O)-alkynyl, CO$_2$-alkynyl, CO$_2$-cycloalkynyl, CO$_2$-alkynyl-cycloalkynyl, CO$_2$-alkynyl-hetero-cyclyl, CO)$_2$-alkynyl-aryl, CO$_2$-alkynyl-heteroaryl, C(O)NH-alkynyl, C(O)NH-eycloalkynyl, C(O)NH-alkynyl-cycloalkynyl, C(O)NH-alkynyl-heterocyclyl, C(O)NH-alkynyl-aryl, C(O)NH-alkynyl-heteroaryl, C(O)N(alkynyl)$_2$, C(O)N(cycloalkynyl)$_2$, SO-alkynyl, SO$_2$-alkynyl, SO$_2$NH-alkynyl, SO$_2$O-alkynyl, alkynyl, or cycloalkynyl substituents, (vi) unsubstituted or substituted heteroaryl, where the heteroaryl radical may have one or more identical or different F, Cl, Br, I, CF$_3$, CN, NH$_2$, NH-alkyl, NH-cycloalkyl, NH-heterocyclyl, NH-aryl, NH-heteroaryl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHSO$_2$-alkyl, NHSO$_2$-aryl, NHSO$_2$-heteroaryl, NO$_2$, SH, S-alkyl, S-aryl, OH, OCF$_3$, O-alkyl, O-cycloalkyl, O-heterocyclyl, O-aryl, O-heteroaryl, OC(O)-alkyl, OC(O)-cycloalkyl, OC(O)-heterocyclyl, OC(O)-aryl, OC(O)-heteroaryl, OSO$_2$-alkyl, OSO$_2$-cycloalkyl, OSO$_2$-aryl, OSO$_2$-heteroaryl, C(O)-alkyl, C(O)-aryl, C(O)-heteroaryl, CO$_2$H, CO$_2$-alkyl, CO$_2$-cycloalkyl, CO$_2$-heterocyclyl, CO2-aryl, CO$_2$-heteroaryl, CO$_2$-alkyl-cycloalkyl, CO$_2$-alkyl-heterocyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO$_2$-alkyl, SO$_2$-aryl, SO$_2$NH$_2$, SO$_2$NH-alkyl, SO$_2$NH-aryl, SO$_2$NH-heteroaryl, SO$_3$H, SO$_2$O-alkyl, SO$_2$O-aryl, SO$_2$O-heteroaryl, alkyl, cycloalkyl, heterocyclyl, aryl, heteroaryl, NH-alkenyl-cycloalkenyl, NH-alkenyl-heterocylyl, NH-alkenyl-aryl, NH-alkenyl-heteroaryl, NH-alkenyl-NH$_2$, NH-alkenyl-OH, N(alkenyl)$_2$, NHC(O)-alkenyl, NHC(O)-cycloalkenyl, NHSO$_2$-alkenyl, S-alkenyl, S-cycloalkenyl, O-alkenyl, O-cycloalkenyl, O-alkenyl-cycloalkenyl, O-alkenyl-heterocyclyl, O-alkenyl-aryl, O-alkenyl-heteroaryl, O-alkenyl-OH, OC(O)-alkenyl, OC(O)-cycloalkenyl, OSO$_2$-alkenyl, OSO$_2$-cycloalkenyl, C(O)-alkenyl, CO$_2$-alkenyl, CO$_2$-cycloalkenyl, CO$_2$-alkenyl-cycloalkenyl, CO$_2$-alkenyl-hetero-cyclyl, CO$_2$-alkenyl-aryl, CO$_2$-alkenyl-heteroaryl, C(O)NH-alkenyl, C(O)NH-cycloalkenyl, C(O)NH-alkenyl-cycloalkenyl, C(O)NH-alkenyl-heterocyclyl, C(O)NH-alkenyl-aryl, C(O)NH-alkenyl-heteroaryl, C(O)N(alkenyl)$_2$, C(O)N(cycloalkenyl)$_2$, SO-alkenyl, SO$_2$-alkenyl, SO$_2$NH-alkenyl, SO$_2$O-alkenyl, SO$_2$O-aryl, alkenyl, cycloalkenyl, NH-alkynyl-cycloalkynyl, NH-alkynyl-heterocyclyl, NH-alkynyl-aryl, NH-alkynyl-heteroaryl, NH-alkynyl-NH$_2$, NH-alkynyl-OH, N(alkynyl)$_2$, NHC(O)-alkynyl, NHC(O)-cycloalkynyl, NHSO$_2$-alkynyl, S-alkynyl, S-cycloalkynyl, O-alkynyl, O-cycloalkynyl, O-alkynyl-cycloalkynyl, O-alkynyl-heterocyclyl, O-alkynyl-aryl, O-alkynyl-heteroaryl, O-alkynyl-OH, OC(O)-alkynyl, OC(O)-cycloalkynyl, OSO$_2$-alkynyl, OSO$_2$-cycloalkynyl, C(O)-alkynyl, CO$_2$-alkynyl, CO$_2$-cycloalkynyl, CO$_2$-alkynyl-cycloalkynyl, CO$_2$-alkynyl-hetero-cyclyl, CO$_2$-alkynyl-aryl, CO$_2$-alkynyl-heteroaryl, C(O)NH-alkynyl, C(O)NH-cycloalkynyl, C(O)NH-alkynyl-cycloalkynyl, C(O)NH-alkynyl-heterocyclyl, C(O)NH-alkynyl-aryl, C(O)NH-alkynyl-heteroaryl, C(O)N(alkynyl)$_2$, C(O)N(cycloalkynyl)$_2$, SO-alkynyl, SO$_2$-alkynyl, SO$_2$NH-alkynyl, SO$_2$O-alkynyl, alkynyl, or cycloalkynyl substituents, (vii) or R4 and R5 together are cycloalkyl cycloalkenyl, cycloalkynyl or heterocyclyl;

(B) is —C(Y)NR6R7, where Y is NH and R6 and R7 are independently of one another (i) hydrogen, (ii) unsubstituted or substituted alkyl, alkenyl or alkynyl, where the alkyl, the alkenyl or the alkynyl radical may have one or more identical or different F, Cl, Br, I, CF$_3$, CN, NH$_2$, NH-alkyl, NH-cycloalkyl, NH-heterocyclyl, NH-aryl, NH-hetero-aryl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHSO$_2$-alkyl, NHSO$_2$-cycloalkyl, NHSO$_2$-aryl, NHSO$_2$-heteroaryl, NO$_2$, SH, S-alkyl, S-cycloalkyl, S-heterocyclyl, S-aryl, S-heteroaryl, OH, OCF$_3$, O-alkyl, O-cycloalkyl, O-heterocyclyl, O-aryl, O-heteroaryl, O-alkyl-cycloalkyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OSO$_2$-alkyl, OSO$_2$-cycloalkyl, OSO$_2$-aryl, OSO$_2$-heteroaryl, C(O)-alkyl, C(O)-aryl, CO$_2$H, CO$_2$-alkyl, CO$_2$-cycloalkyl, CO2-heterocyclyl, CO$_2$-aryl, CO2-heteroaryl, CO$_2$-alkyl-cycloalkyl, CO$_2$-alkylheterocyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-hetero-cyclyl, C(O)NH-alkyl-aryl, C(O)NH-alkyl-hetero-aryl, C(O)N(alkyl)$_2$, C(O)N(cycloalkyl)$_2$, C(O)N(aryl)$_2$, C(O)N(heteroaryl)$_2$, SO-alkyl, SO-aryl, SO$_2$-alkyl, SO$_2$-aryl, SO$_2$NH$_2$, SO$_3$H, alkyl, cycloalkyl, heterocyclyl, aryl, heteroaryl, NH-alkenyl-cycloalkenyl, NH-alkenyl-heterocyclyl, NH-alkenyl-aryl, NH-alkenyl-heteroaryl, NH-alkenyl-NH$_2$, NH-alkenyl-OH, N(alkenyl)$_2$, NHC(O)-alkenyl, NHC(O)-cycloalkenyl, NHSO$_2$-alkenyl, S-alkenyl, S-cycloalkenyl, O-alkenyl, O-cycloalkenyl, O-alkenyl-cycloalkenyl, O-alkenyl-heterocyclyl, O-alkenyl-aryl, O-alkenyl-heteroaryl, O-alkenyl-OH, OC(O)-alkenyl, OC(O)-cycloalkenyl, OSO$_2$-alkenyl, OSO$_2$cycloalkenyl, C(O)-alkenyl, CO$_2$-alkenyl, CO$_2$-cycloalkenyl, CO$_2$-alkenyl-cycloalkenyl, CO$_2$-alkenyl-hetero-cyclyl, CO$_2$-alkenyl-aryl, CO$_2$-alkenyl-heteroaryl, C(O)NH-alkenyl, C(O)NH-cycloalkenyl, C(O)NH-alkenyl-cycloalkenyl, C(O)NH-alkenyl-heterocyclyl, C(O)NH-alkenyl-aryl, C(O)NH-alkenyl-heteroaryl, C(O)N(alkenyl)$_2$, C(O)N(cycloalkenyl)$_2$, SO-alkenyl, SO$_2$-alkenyl, SO$_2$NH-alkenyl, SO$_2$O-alkenyl, SO$_2$O-aryl, alkenyl, cycloalkenyl, NH-alkynyl-cycloalkynyl, NH-alkynyl-heterocyclyl, NH-alkynyl-aryl, NH-alkynyl-heteroaryl, NH-alkynyl-NH$_2$, NH-alkynyl-OH, N(alkynyl)$_2$, NHC(O)-alkynyl, NHC(O)-cycloalkynyl, NHSO$_2$-alkynyl, S-alkynyl, S-cycloalkynyl, O-alkynyl, O-cycloalkynyl, O-alkynyl-cycloalkynyl, O-alkynyl-heterocyclyl, O-alkynyl-aryl, O-alkynyl-heteroaryl, O-alkynyl-OH, OC(O)-alkynyl, OC(O)-cycloalkynyl, OSO$_2$-alkynyl, OSO$_2$-cycloalkynyl, C(O)-alkynyl, CO$_2$-alkynyl, CO$_2$-cycloalkynyl, CO$_2$-alkynyl-cycloalkynyl, CO$_2$-alkynyl-hetero-cyclyl, CO$_2$-alkynyl-aryl, CO$_2$-alkynyl-heteroaryl, C(O)NH-alkynyl, C(O)NH-cycloalkynyl, C(O)NH-alkynyl-cycloalkynyl, C(O)NH-alkynyl-heterocyclyl, C(O)NH-alkynyl-aryl, C(O)NH-alkynyl-heteroaryl, C(O)N(alkynyl)$_2$, C(O)N(cycloalkynyl)$_2$, SO-alkynyl, SO$_2$-alkynyl, SO$_2$NH-alkynyl, SO$_2$O-alkynyl, alkynyl, or cycloalkynyl substituents, (iii) unsubstituted or substituted cycloalkyl, cycloalkenyl or cycloalkynyl, where the cycloalkyl, the cycloalkenyl or the cycloalkynyl radical may have one or more identical or different F, Cl, Br, I, NH$_2$, NH-alkyl, NH-cycloalkyl, NH-heterocyclyl, NH-aryl, NH-heteroaryl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHSO$_2$-alkyl, NHSO$_2$-cycloalkyl, NHSO$_2$-aryl, NHSO$_2$-heteroaryl, OH, O-alkyl, O-cycloalkyl, O-heterocyclyl, O-aryl, O-heteroaryl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OSO$_2$-alkyl, OSO$_2$-cycloalkyl, OSO$_2$-aryl, OSO$_2$-heteroaryl, CO$_2$H, CO$_2$-alkyl, CO$_2$-cycloalkyl, CO$_2$-heterocyclyl, CO$_2$-aryl, CO$_2$-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-aryl, C(O)NH-alkyl-heteroaryl, C(O)N(alkyl)$_2$, alkyl, aryl, NH-cycloalkenyl, NH-alkenyl-aryl, NH-alkenyl-heteroaryl, N(alkenyl)$_2$, NHC(O)-alkenyl, NHC(O)-cycloalkenyl, NHSO₂-alkenyl, NHSO₂-cycloalkenyl, O-alkenyl, O-cycloalkenyl, O-alkenyl-aryl, O-alkenyl-heteroaryl, OC(O)-alkenyl, OC(O)-cycloalkenyl, OSO₂-alkenyl, OSO₂-cycloalkenyl, CO₂-alkenyl, CO₂-cycloalkenyl, C(O)NH-alkenyl, C(O)NH-cycloalkenyl, C(O)NH-alkenyl-aryl, C(O)NH-alkenyl-heteroaryl, C(O)N(alkenyl)₂, alkenyl, NH-cycloalkynyl, NH-alkynyl-aryl, NH-alkynyl-heteroaryl, N(alkynyl)₂, NHC(O)-alkynyl, NHC(O)-cycloalkynyl, NHSO₂-alkynyl, NHSO₂-cycloalkynyl, NHSO₂-aryl, O-alkynyl, O-cycloalkynyl, O-alkynyl-aryl, O-alkynyl-heteroaryl, OC(O)-alkynyl, OC(O)-cycloalkynyl, OSO₂-alkynyl, OSO₂-cycloalkynyl, CO₂-alkynyl, CO₂-cycloalkynyl, C(O)NH-alkynyl, C(O)NH-cycloalkynyl, C(O)NH-alkynyl-aryl, C(O)NH-alkynyl-heteroaryl, C(O)N(alkynyl)₂, or alkynyl substituents, (iv) unsubstituted or substituted heterocyclyl, where the heterocyclyl radical may have one or more identical or different OH, O-alkyl, O-aryl, NH-alkyl, NH-aryl, alkyl, aryl, O-alkynyl, NH-alkynyl, alkynyl, O-alkenyl, NH-alkenyl, or alkenyl substituents, (v) unsubstituted or substituted aryl, where the aryl radical may have one or more identical or different F, Cl, Br, I, OF₃, CN, NH₂, NH-alkyl, NH-cycloalkyl, NH-heterocyclyl, NH-aryl, NH-heteroaryl, NH-alkyl-cycloalkyl, NH-alkylheterocyclyl, NH-alkyl-aryl, NH-alkyl-heteroaryl, NH-alkyl-NH₂, NH-alkyl-OH, N(alkyl)₂, NHC(O)-alkyl, NHC(O)-cycloalkyl, NHC(O)-heterocyclyl, NHC(O)-aryl, NHC(O)-heteroaryl, NHSO₂-alkyl, NHSO₂-aryl, NHSO₂-heteroaryl, NO₂, SH, S-alkyl, S-cycloalkyl, S-heterocyclyl, S-aryl, S-heteroaryl, OH, OCF₃, O-alkyl, O-cycloalkyl, O-heterocyclyl, O-aryl, O-heteroaryl, O-alkyl-cycloalkyl, O-alkylheterocyclyl, O-alkyl-aryl, O-alkyl-heteroaryl, O-alkyl-OH, OC(O)-alkyl, OC(O)-cycloalkyl, OC(O)-heterocyclyl, OC(O)-aryl, OC(O)-heteroaryl, OSO₂-alkyl, OSO₂-cycloalkyl, OSO₂-aryl, OSO₂-heteroaryl, C(O)-alkyl, C(O)-aryl, C(O)-heteroaryl, CO₂H, CO₂-alkyl, CO₂-cycloalkyl, CO₂-heterocyclyl, CO₂-aryl, CO₂-heteroaryl, CO₂-alkyl-cycloalkyl, CO₂-alkyl-heterocyclyl, CO₂-alkyl-aryl, CO₂-alkyl-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)₂, C(O)N(cycloalkyl)₂, C(O)N(aryl)₂, C(O)N(heteroaryl)₂, SO-alkyl, SO-aryl, SO₂-alkyl, SO₂-aryl, SO₂NH₂, SO₂NH-alkyl, SO₂NH-aryl, SO₂NH-heteroaryl, SO₃H, SO₂O-alkyl, SO₂O-aryl, SO₂O-heteroaryl, alkyl, cycloalkyl, heterocyclyl, aryl, heteroaryl, NH-alkenyl-cycloalkenyl, NH-alkenyl-heterocyclyl, NH-alkenyl-aryl, NH-alkenyl-heteroaryl, NH-alkenyl-NH₂, NH-alkenyl-ON, N(alkenyl)₂, NHC(O)-alkenyl, NHC(O)-cycloalkenyl, NHSO₂-alkenyl, S-alkenyl, S-cycloalkenyl, O-alkenyl, O-cycloalkenyl, O-alkenyl-cycloalkenyl, O-alkenyl-heterocyclyl, O-alkenyl-aryl, O-alkenyl-heteroaryl, O-alkenyl-OH, OC(O)-alkenyl, OC(O)-cycloalkenyl, OSO₂-alkenyl, OSO₂-cycloalkenyl, C(O)-alkenyl, CO₂-alkenyl, CO₂-cycloalkenyl, CO₂-alkenyl-cycloalkenyl, CO₂-alkenyl-hetero-cyclyl, CO₂-alkenyl-aryl, CO₂-alkenyl-heteroaryl, C(O)NH-alkenyl, C(O)NH-cycloalkenyl, C(O)NH-alkenyl-cycloalkenyl, C(O)NH-alkenyl-heterocyclyl, C(O)NH-alkenyl-aryl, C(O)NH-alkenyl-heteroaryl, C(O)N(alkenyl)₂, C(O)N(cycloalkenyl)₂, SO-alkenyl, SO₂-alkenyl, SO₂NH-alkenyl, SO₂O-alkenyl, SO₂O-aryl, alkenyl, cycloalkenyl, NH-alkynyl-cycloalkynyl, NH-alkynyl-heterocyclyl, NH-alkynyl-aryl, NH-alkynyl-heteroaryl, NH-alkynyl-NH₂, NH-alkynyl-OH, N(alkynyl)₂, NHC(O)-alkynyl, NHC(O)-cycloalkynyl, NHSO₂-alkynyl, S-alkynyl, S-cycloalkynyl, O-alkynyl, O-cycloalkynyl, O-alkynyl-cycloalkynyl, O-alkynyl-heterocyclyl, O-alkynyl-aryl, O-alkynyl-heteroaryl, O-alkynyl-OH, OC(O)-alkynyl, OC(O)-cycloalkynyl, OSO₂-alkynyl, OSO₂-cycloalkynyl, C(O)-alkynyl, CO₂-alkynyl, CO₂-cycloalkynyl, CO₂-alkynyl-cycloalkynyl, CO₂-alkynyl-hetero-cyclyl, CO₂-alkynyl-aryl, CO₂-alkynyl-heteroaryl, C(O)NH-alkynyl, C(O)NH-cycloalkynyl, C(O)NH-alkynyl-cycloalkynyl, C(O)NH-alkynyl-heterocyclyl, C(O)NH-alkynyl-aryl, C(O)NH-alkynyl-heteroaryl, C(O)N(alkynyl)₂, C(O)N(cycloalkynyl)₂, SO-alkynyl, SO₂-alkynyl, SO₂NH-alkynyl, SO₂O-alkynyl, alkynyl, or cycloalkynyl substituents, (vi) unsubstituted or substituted heteroaryl, where the heteroaryl radical may have one or more identical or different F, Cl, Br, I, CF₂, CN, NH₂, NH-alkyl, NH-cycloalkyl, NH-heterocyclyl, NH-aryl, NH-heteroaryl, NH-alkyl-aryl, NH-alkyl-heteroaryl, N(alkyl)₂, NHC(O)-alkyl, NHC(O)-cycloalkyl, NHC(O)-heterocyclyl, NHC(O)-aryl, NHC(O)-heteroaryl, NHSO₂-alkyl, NHSO₂-aryl, NHSO₂-heteroaryl, NO₂, SH, S-alkyl, S-aryl, OH, OCF₃, O-alkyl, O-cycloalkyl, O-heterocyclyl, O-aryl, O-heteroaryl, OC(O)-alkyl, OC(O)-cycloalkyl, OC(O)-heterocyclyl, OC(O)-aryl, OC(O)-heteroaryl, OSO₂-alkyl, OSO₂-cycloalkyl, OSO₂-aryl, OSO₂-heteroaryl, C(O)-alkyl, C(O)-aryl, C(O)-heteroaryl, CO₂H, CO₂-alkyl, CO₂-cycloalkyl, CO₂-heterocyclyl, CO₂-aryl, CO₂-heteroaryl, CO₂-alkyl-cycloalkyl, CO₂-alkylheterocyclyl, CO₂-alkylaryl, CO₂-alkyl-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)₂, C(O)N(cycloalkyl)₂, C(O)N(aryl)₂, C(O)N(heteroaryl)₂, SO₂-alkyl, SO₂-aryl, SO₂NH₂, SO₂NH-alkyl, SO₂NH-aryl, SO₂NH-heteroaryl, SO₃H, SO₂O-alkyl, SO₂O-aryl, SO₂O-heteroaryl, alkyl, cycloalkyl, heterocyclyl, aryl, heteroaryl, NH-alkenyl-cycloalkenyl, NH-alkenyl-heterocyclyl, NH-alkenyl-aryl, NH-alkenyl-heteroaryl, NHalkenyl-NH₂, NH-alkenyl-OH, N(alkenyl)₂, NHC(O)-alkenyl, NHC(O)-cycloalkenyl, NHSO₂-alkenyl, S-alkenyl, S-cycloalkenyl, O-alkenyl, O-cycloalkenyl, O-alkenyl-cycloalkenyl, O-alkenyl-heterocyclyl, O-alkenyl-aryl, O-alkenyl-heteroaryl, O-alkenyl-OH, OC(O)-alkenyl, OC(O)-cycloalkenyl, OSO₂-alkenyl, OSO₂-cycloalkenyl, C(O)-alkenyl, CO₂-alkenyl, CO₂-cycloalkenyl, CO₂-alkenyl-cycloalkenyl, CO₂-alkenyl-hetero-cyclyl, CO₂-alkenyl-aryl, CO₂-alkenyl-heteroaryl, C(O)NH-alkenyl, C(O)NH-cycloalkenyl, C(O)NH-alkenyl-cycloalkenyl, C(O)NH-alkenyl-heterocyclyl, C(O)NH-alkenyl-aryl, C(O)NH-alkenyl-heteroaryl, C(O)N(alkenyl)₂, C(O)N(cycloalkenyl)₂, SO-alkenyl, SO₂-alkenyl, SO₂NH-alkenyl, SO₂O-alkenyl, SO₂O-aryl, alkenyl, cycloalkenyl, NH-alkynyl-cycloalkynyl, NH-alkynyl-heterocyclyl, NH-alkynyl-aryl, NH-alkyl-heteroaryl, NH-alkynyl-NH$_2$, NH-alkynyl-OH, N(alkynyl)$_2$, NHC(O)-alkynyl, NHC(O)-cycloalkynyl, NHSO$_2$-alkynyl, S-alkynyl, S-cycloalkynyl, O-alkynyl, O-cycloalkynyl, O-alkynyl-cycloalkynyl, O-alkynyl-heterocyclyl, O-alkynyl-aryl, O-alkynyl-heteroaryl, O-alkynyl-OH, OC(O)-alkynyl, OC(O)-cycloalkynyl, OSO$_2$-alkynyl, OSO$_2$-cycloalkynyl, C(O)-alkynyl, CO$_2$-alkynyl, CO$_2$-cycloalkynyl, CO$_2$-alkynyl-cycloalkynyl, CO$_2$-alkynyl-heterocyclyl, CO$_2$-alkynyl-aryl, CO$_2$-alkynyl-heteroaryl, C(O)NH-alkynyl, C(O)NH-cycloalkynyl, C(O)NH-alkynyl-cycloalkynyl, C(O)NH-alkynyl-heterocyclyl, C(O)NH-alkynyl-aryl, C(O)NH-alkynyl-heteroaryl, C(O)N(alkynyl)$_2$, C(O)N(cycloalkynyl)$_2$, SO-alkynyl, SO$_2$-alkynyl, SO$_2$NH-alkynyl, SO$_2$O-alkynyl, alkynyl, or cycloalkynyl substituents, (vii) or R6 and R7 together are cycloalkyl, cycloalkenyl, cycloalkynyl or heterocyclyl;

(C) is —C(NR8)R9 where R8 is H and R9 is (i) unsubstituted or substituted alkyl, alkenyl or alkynyl, where the alkyl, the alkenyl or the alkynyl radical may have one or more identical or different F, Cl, Br, I, CF$_3$, NH$_2$, NH-alkyl, NH-cycloalkyl, NH-heterocyclyl, NH-aryl, NH-hetero-aryl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHSO$_2$-alkyl, NHSO$_2$-cycloalkyl, NHSO$_2$-aryl, NHSO$_2$-heteroaryl, NO$_2$, SH, S-alkyl, S-cycloalkyl, S-heterocyclyl, S-aryl, S-heteroaryl, OH, OCF$_3$, O-alkyl, O-cycloalkyl, O-heterocyclyl, O-aryl, O-heteroaryl, O-alkyl-cycloalkyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OSO$_2$-alkyl, OSO$_2$-cycloalkyl, OSO$_2$-aryl, OSO$_2$-heteroaryl, C(O)-alkyl, C(O)-aryl, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkyl-heterocyclyl, CO$_2$-alkyl-aryl, CO$_2$-alkyl-heteroaryl, C(O)—NH$_2$, C(O)NH-alkyl, C(O)NH-cycloalkyl, C(O)NH heterocyclyl, C(O)NH-aryl, C(O)NH-heteroaryl, C(O)NH-alkyl-cycloalkyl, C(O)NH-alkyl-hetero-cyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, SO$_2$-alkyl, SO$_2$-aryl, SO$_2$NH$_2$, SO$_3$H, alkyl, cycloalkyl, heterocyclyl, aryl, heteroaryl, NH-alkenyl-cycloalkenyl, NH-alkenyl-heterocyclyl, NH-alkenyl-aryl, NH-alkenyl-heteroaryl, NH-alkenyl-NH$_2$, NH-alkenyl-OH, N(alkenyl)$_2$, NHC(O)-alkenyl, NHC(O)-cycloalkenyl, NHSO$_2$-alkenyl, S-alkenyl, S-cycloalkenyl, O-alkenyl, O-cycloalkenyl, O-alkenyl-cycloalkenyl, O-alkenyl-heterocyclyl, O-alkenyl-aryl, O-alkenyl-heteroaryl, O-alkenyl-OH, OC(O)-alkenyl, OC(O)-cycloalkenyl, OSO$_2$-alkenyl, OSO$_2$-cycloalkenyl, C(O)-alkenyl, CO$_2$-alkenyl, CO$_2$-cycloalkenyl, CO$_2$-alkenyl-cycloalkenyl, CO$_2$-alkenyl-hetero-cyclyl, CO$_2$-alkenyl-aryl, CO$_2$-alkenyl-heteroaryl, C(O)NH-alkenyl, C(O)NH-cycloalkenyl, C(O)NH-alkenyl-cycloalkenyl, C(O)NH-alkenyl-heterocyclyl, C(O)NH-alkenyl-aryl, C(O)NH-alkenyl-heteroaryl, C(O)N(alkenyl)$_2$, C(O)N(cycloalkenyl)$_2$, SO-alkenyl, SO$_2$-alkenyl, SO$_2$NH-alkenyl, SO$_2$O-alkenyl, SO$_2$O-aryl, alkenyl, cycloalkenyl, NH-alkynyl-cycloalkynyl, NH-alkynyl-heterocyclyl, NH-alkynyl-aryl, NH-alkynyl-heteroaryl, NH-alkynyl-NH$_2$, NH-alkynyl-OH, N(alkynyl)$_2$, NHC(O)-alkynyl, NHC(O)-cycloalkynyl, NHSO$_2$-alkynyl, S-alkynyl, S-cycloalkynyl, O-alkynyl, O-cycloalkynyl, O-alkynyl-cycloalkynyl, O-alkynyl-heterocyclyl, O-alkynyl-aryl, O-alkynyl-heteroaryl, O-alkynyl-OH, OC(O)-alkynyl, OC(O)-cycloalkynyl, OSO$_2$-alkynyl, OSO$_2$-cycloalkynyl, C(O)-alkynyl, CO$_2$-alkynyl, CO$_2$-cycloalkynyl, CO)$_2$-alkynyl-cycloalkynyl, CO$_2$-alkynyl-hetero-cyclyl, CO$_2$-alkynyl-aryl, CO$_2$-alkynyl-heteroaryl, C(O)NH-alkynyl, C(O)NH-cycloalkynyl, C(O)NH-alkynyl-cycloalkynyl, C(O)NH-alkynyl-heterocyclyl, C(O)NH-alkynyl-aryl, C(O)NH-alkynyl-heteroaryl, C(O)N(alkynyl)$_2$, C(O)N(cycloalkynyl)$_2$, SO-alkynyl, SO$_2$-alkynyl, SO$_2$NH-alkynyl, SO$_2$O-alkynyl, alkynyl, or cycloalkynyl substituents, (ii) unsubstituted or substituted cycloalkyl, cycloalkenyl or cycloalkynyl, where the cycloalkyl, the cycloalkenyl or the cycloalkynyl radical may have one or more identical or different F, Cl, Br, I, NH$_2$, NH-alkyl, NH-cycloalkyl, NH-heterocyclyl, NH-aryl, NH-hetero-aryl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHSO$_2$-alkyl, NHSO$_2$-cycloalkyl, NHSO$_2$-aryl, NHSO$_2$-heteroaryl, OH, O-alkyl, O-cycloalkyl, O-heterocyclyl, O-aryl, O-heteroaryl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OSO$_2$-alkyl, OSO$_2$-cycloalkyl, OSO$_2$-aryl, OSO$_2$-heteroaryl, CO$_2$H, CO$_2$-alkyl, CO$_2$-cycloalkyl, CO$_2$-heterocyclyl, CO$_2$-aryl, CO$_2$-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-aryl, C(O)NH-alkyl-heteroaryl, C(O)N(alkyl)$_2$, alkyl, aryl, NH-cycloalkenyl, NH-alkenyl-aryl, NH-alkenyl-heteroaryl, N(alkenyl)$_2$, NHC(O)-alkenyl, NHC(O)-cycloalkenyl, NHSO$_2$-alkenyl, NHSO$_2$-cycloalkenyl, O-alkenyl, O-cycloalkenyl, O-alkenyl-aryl, O-alkenyl-heteroaryl, OC(O)-alkenyl, OC(O)-cycloalkenyl, OSO$_2$-alkenyl, OSO$_2$-cycloalkenyl, CO$_2$-alkenyl, CO$_2$-cycloalkenyl, C(O)NH-alkenyl, C(O)NH-cycloalkenyl, C(O)NH-alkenyl-aryl, C(O)NH-alkenyl-heteroaryl, C(O)N(alkenyl)$_2$, alkenyl, NH-cycloalkynyl, NH-alkynyl-aryl, NH-alkynyl-heteroaryl, N(alkynyl)$_2$, NHC(O)-alkynyl, NHC(O)-cycloalkynyl, NHSO$_2$-alkynyl, NHSO$_2$-cycloalkynyl, NHSO$_2$-aryl, O-alkynyl, O-cycloalkynyl, O-alkynyl-aryl, O-alkynyl-heteroaryl, OC(O)-alkynyl, OC(O)-cycloalkynyl, OSO$_2$-alkynyl, OSO$_2$-cycloalkynyl, CO$_2$-alkynyl, CO$_2$-cycloalkynyl, C(O)NH-alkynyl, C(O)NH-cycloalkynyl, C(O)NH-alkynyl-aryl, C(O)NH-alkynyl-heteroaryl, C(O)N(alkynyl)$_2$, or alkynyl substituents, (iii) unsubstituted or substituted heterocyclyl, where the heterocyclyl radical may have one or more identical or different OH, O-alkyl, O-aryl, NH-alkyl, NH-aryl, alkyl, aryl, O-alkynyl, NH-alkynyl, alkynyl, O-alkenyl, NH-alkenyl, or alkenyl substituents, (iv) unsubstituted or substituted aryl, where the aryl radical may have one or more identical or different F, Cl, Br, I, CF$_3$, NH$_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-NH$_2$, NH-alkyl-OH, N(alkyl)$_2$, NHC(O)-alkyl, NHC(O)-cycloalkyl, NHC(O)heterocyclyl, NHC(O)-aryl, NHC(O)-heteroaryl, NHSO$_2$-alkyl, NHSO$_2$-aryl, NHSO$_2$-heteroaryl, NO$_2$, SH, S-alkyl, S-cycloalkyl, S-heterocyclyl, S-aryl, S-heteroaryl, OH, OCF$_3$, O-alkyl, O-cycloalkyl, O-heterocyclyl, O-aryl, O-heteroaryl, O-alkyl-cycloalkyl, O-alkylheterocyclyl, O-alkyl-aryl, O-alkyl-heteroaryl, O-alkyl-OH, OC(O)-alkyl, OC(O)-cycloalkyl, OC(O)-heterocyclyl, OC(O)-aryl, OC(O)-heteroaryl, OSO$_2$-alkyl OSO$_2$-cycloalkyl, OSO$_2$-aryl, OSO$_2$-heteroaryl, C(O)-alkyl, C(O)-aryl, C(O)-heteroaryl, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkylheterocyclyl, CO$_2$-alkyl-aryl, CO$_2$-alkyl-heteroaryl, C(O)—NH2, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, SO$_2$-alkyl, SO$_2$-aryl, SO$_2$NH$_2$, SO$_2$NH-alkyl, SO$_2$NH-aryl, SO$_2$NH-heteroaryl, SO$_3$H, SO$_2$O-alkyl, SO$_2$O-aryl, SO$_2$O-heteroaryl, alkyl, cycloalkyl, heterocyclyl, aryl, heteroaryl, NH-alkenyl-cycloalkenyl, NH-alkenyl-heterocyclyl, NH-alkenyl-aryl, NH-alkenyl-heteroaryl, NHalkenyl-NH$_2$, NH-alkenyl-OH, N(alkenyl)$_2$, NHC(O)-alkenyl, NHC(O)-cycloalkenyl, NHSO$_2$-alkenyl, S-alkenyl, S-cycloalkenyl, O-alkenyl, O-cycloalkenyl, O-alkenyl-cycloalkenyl, O-alkenyl-heterocyclyl, O-alkenyl-aryl, O-alkenyl-heteroaryl, O-alkenyl-OH, OC(O)-alkenyl, OC(O)-cycloalkenyl, OSO$_2$-alkenyl, OSO$_2$-cycloalkenyl, C(O)-alkenyl, CO$_2$-alkenyl, CO$_2$-cycloalkenyl, CO$_2$-alkenyl-cycloalkenyl, CO$_2$-alkenyl-hetero-cyclyl, CO$_2$-alkenyl-aryl, CO$_2$-alkenyl-heteroaryl, C(O)NH-alkenyl, C(O)NH-cycloalkenyl, C(O)NH-alkenyl-cycloalkenyl, C(O)NH-alkenyl-heterocyclyl, C(O)NH-alkenyl-aryl, C(O)NH-alkenyl-heteroaryl, C(O)N(alkenyl)$_2$, C(O)N(cycloalkenyl)$_2$, SO-alkenyl, SO$_2$-alkenyl, SO$_2$NH-alkenyl, SO$_2$O-alkenyl, SO$_2$O-aryl, alkenyl, cycloalkenyl, NH-alkynyl-cycloalkynyl, NH-alkynyl-heterocyclyl, NH-alkynyl-aryl, NH-alkynyl-heteroaryl, NH-alkynyl-NH$_2$, NH-alkynyl-OH, N(alkynyl)$_2$, NHC(O)-alkynyl, NHC(O)-cycloalkynyl, NHSO$_2$-alkynyl, S-alkynyl, S-cycloalkynyl, O-alkynyl, O-cycloalkynyl, O-alkynyl-cycloalkynyl, O-alkynyl-heterocyclyl, O-alkynyl-aryl, O-alkynyl-heteroaryl, O-alkynyl-OH, OC(O)-alkynyl, OC(O)-cycloalkynyl, OSO$_2$-alkynyl, OSO$_2$-cycloalkynyl, C(O)-alkynyl, CO$_2$-alkynyl, CO$_2$-cycloalkynyl, CO$_2$-alkynyl-cycloalkynyl, CO$_2$-alkynyl-hetero-cyclyl, CO$_2$-alkynyl-aryl, CO$_2$-alkynyl-heteroaryl, C(O)NH-alkynyl, C(O)NH-cycloalkynyl, C(O)NH-alkynyl-cycloalkynyl, C(O)NH-alkynyl-heterocyclyl, C(O)NH-alkynyl-aryl, C(O)NH-alkynyl-heteroaryl, C(O)N(alkynyl)$_2$, C(O)N(cycloalkynyl)$_2$, SO-alkynyl, SO$_2$-alkynyl, SO$_2$NH-alkynyl, SO$_2$O-alkynyl, alkynyl, or cycloalkynyl substituents; or a physiologically tolerated salt, or hydrate thereof.

2. The compound according to claim 1, wherein
(i) R1, R2, R4, R5, R6, R7, and R9, independently of one another, are alkyl radicals selected from methyl, ethyl, n-propyl, 2-propyl, n-butyl, sec-butyl, tert-butyl, n-pentyl, iso-pentyl, neo-pentyl, n-hexyl, 2-hexyl, and n-octyl;
(ii) R1, R2, R4, R5, R6, R7, and R9, independently of one another, are alkenyl radicals selected from ethylenyl (vinyl), propenyl (—CH$_2$CH=CH$_2$; —CH=CH—CH$_3$, —C(=CH$_2$)—CH$_3$), butenyl, pentenyl, hexenyl, heptenyl, and octenyl; or (iii) R5, R6, R7, R8, R9, R11, R12, R13, R14, R16, and R17, independently of one another, are alkynyl radicals selected from ethynyl, propynyl (—CH$_2$—C≡CH, —C≡C—CH$_3$), butynyl, pentynyl, hexynyl, heptynyl, and octynyl.

3. The compound according to claim 1, wherein R1, R2, R4, R5, R6, R7, and R9, (R4 and R5 together), (R6 and R7 together), independently of one another, are heterocylyl radicals selected from tetrahydrofuryl, tetrahydropyranyl, pyrrolidinyl, piperidinyl, piperazinyl and morpholinyl.

4. The compound according to claim 1, wherein R1, R2, R4, R5, R6, R7, and R9, (R4 and R5 together), (R6 and R7 together), independently of one another, are heteroaryl radicals selected from pyrrolyl, furyl, thienyl, thiazolyl, oxazolyl, isoxazolyl, pyrazolyl, imidazolyl, pyridinyl, pyrimidinyl, pyridazinyl, pyrazinyl, phthalazinyl, indolyl, indazolyl, indolizinyl, quinolinyl, isoquinolinyl, quinoxalinyl, quinazolinyl, carbazolyl, phenaziriyl, phenothiazinyl, and acridinyl.

5. The compound according to claim 1 having at least one asymmetric carbon atom in the form of a racemate, an enantiomer, a diastereomer, a tautomer or a mixture thereof.

6. The compound according to claim 1, which is one of the following compounds:

1-allyl-3-(3-phenylpyrido[2,3-b]pyrazin-6-yl)thiourea;
1-allyl-3-(3-naphthalen-2-ylpyrido[2,3-b]pyrazin-6-yl)thiourea;
1-allyl-3-[3-(4-methoxyphenyl)pyrido[2,3-b]pyrazin-6-yl]thiourea;
1-allyl-3-[3-(4-hydroxyphenyl)pyrido[2,3-b]pyrazin-6-yl]thiourea hydrochloride;
1-(2-methylallyl)-3-(3-phenylpyrido[2,3-b]pyrazin-6-yl)thiourea;
1-(2-methylallyl)-3-(3-naphthalen-2-ylpyrido[2,3-b]pyrazin-6-yl)thiourea;
1-[3-(4-methoxyphenyl)pyrido[2,3-b]pyrazin-6-yl)-3-(2-methylallyl)thiourea;
1-(3-naphthalen-2-ylpyrido[2,3-b]pyrazin-6-yl)-3-(4-nitrophenyl)thiourea;
1-[3-(4-methoxyphenyl)pyrido[2,3-b]pyrazin-6-yl]-3-(4-nitrophenyl)thiourea;
1-tert-butyl-3-(3-phenylpyrido[2,3-b]pyrazin-6-yl)thiourea;
1-cyclopropyl-3-(3-phenylpyrido[2,3-b]pyrazin-6-yl)thiourea;
1-methyl-3-(3-phenylpyrido[2,3-b]pyrazin-6-yl)thiourea;
1-benzyl-3-(3-phenylpyrido[2,3-b]pyrazin-6-yl)thiourea;
1-(4-fluorophenyl)-3-(3-phenylpyrido[2,3-b]pyrazin-6-yl)thiourea;
1-(3-phenylpyrido[2,3-b]pyrazin-6-yl)-3-p-tolylurea;
1-(4-chloro-3-trifluoromethylphenyl)-3-(3-phenylpyrido[2,3-b]pyrazin-6-yl)urea; or
1-(2-morpholin-4-ylethyl)-3-(3-phenylpyrido[2,3-b]pyrazin-6-yl)urea.

7. A pharmaceutical composition, comprising one or more compounds according to claim 1, and a pharmaceutically acceptable carrier, diluent or other excipient.

8. A process for producing the pharmaceutical composition according to claim 1, comprising combining one or more compounds according to claim 1 with one or more pharmaceutically acceptable carriers, diluents or other excipients.

* * * * *